United States Patent
Ho et al.

(10) Patent No.: US 10,765,487 B2
(45) Date of Patent: Sep. 8, 2020

(54) SYSTEMS AND METHODS FOR DOCKING MEDICAL INSTRUMENTS

(71) Applicant: Auris Health, Inc., Redwood City, CA (US)

(72) Inventors: Mingyen Ho, Santa Clara, CA (US); Chauncey F. Graetzel, Palo Alto, CA (US); Adrian Hairrell, San Francisco, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/586,527

(22) Filed: Sep. 27, 2019

(65) Prior Publication Data
US 2020/0100853 A1  Apr. 2, 2020

Related U.S. Application Data

(60) Provisional application No. 62/738,483, filed on Sep. 28, 2018.

(51) Int. Cl.
*H02P 7/00* (2016.01)
*A61B 34/30* (2016.01)
(Continued)

(52) U.S. Cl.
CPC .............. *A61B 34/30* (2016.02); *A61B 34/71* (2016.02); *A61B 2017/00477* (2013.01);
(Continued)

(58) Field of Classification Search
CPC ...... H02P 7/00; A61B 34/30; A61B 2034/301
See application file for complete search history.

(56) References Cited

U.S. PATENT DOCUMENTS

| 4,644,237 A | 2/1987 | Frushour et al. |
| 4,745,908 A | 5/1988 | Wardle |

(Continued)

FOREIGN PATENT DOCUMENTS

| CN | 1511249 | 7/2004 |
| CN | 103565529 | 2/2014 |

(Continued)

OTHER PUBLICATIONS

Blankenstein, Jun. 2008, Dynamic Registration and High Speed Visual Servoing in Robot-Assisted Surgery, Katholieke Universiteit Leuven, Leuven, Belgium.

(Continued)

*Primary Examiner* — Cortez M Cook
(74) *Attorney, Agent, or Firm* — Knobbe Martens Olson & Bear LLP

(57) ABSTRACT

Certain aspects relate to systems and techniques for docking medical instruments. For example, a medical system can include an instrument drive mechanism having a drive output that rotates and engages a corresponding drive input on a robotic medical instrument, a motor configured to rotate the drive output, and a torque sensor configured to measure torque imparted on the drive output. The robotic medical instrument can include a pre-tensioned pull wire actuated by the drive input. The system can activate the motor associated with the drive output to rotate the drive output in response to a torque signal from the torque sensor associated with the drive output in order to align the drive output with the drive input.

30 Claims, 30 Drawing Sheets

(51) Int. Cl.
*A61B 34/00* (2016.01)
*A61B 17/00* (2006.01)
*A61B 90/00* (2016.01)

(52) U.S. Cl.
CPC ... *A61B 2034/301* (2016.02); *A61B 2034/302* (2016.02); *A61B 2034/303* (2016.02); *A61B 2090/066* (2016.02); *A61B 2562/0261* (2013.01)

(56) References Cited

U.S. PATENT DOCUMENTS

| | | |
|---|---|---|
| 4,748,969 A | 6/1988 | Wardle |
| 5,194,791 A | 3/1993 | Cull |
| 5,251,611 A | 10/1993 | Zehel et al. |
| 5,280,781 A | 1/1994 | Oku |
| 5,408,263 A | 4/1995 | Kikuchi |
| 5,669,876 A | 9/1997 | Schechter et al. |
| 5,672,877 A | 9/1997 | Liebig et al. |
| 5,899,851 A | 5/1999 | Koninckx |
| 6,004,016 A | 12/1999 | Spector |
| 6,198,974 B1 | 3/2001 | Webster, Jr. |
| 6,246,200 B1 | 6/2001 | Blumenkranz et al. |
| 6,459,926 B1 | 10/2002 | Nowlin |
| 6,690,963 B2 | 2/2004 | Ben-Haim |
| 6,837,846 B2 | 1/2005 | Jaffe |
| 7,197,354 B2 | 3/2007 | Sobe |
| 7,607,440 B2 | 10/2009 | Coste-Maniere et al. |
| 7,763,015 B2 | 7/2010 | Cooper et al. |
| 7,772,541 B2 | 8/2010 | Froggatt et al. |
| 7,963,288 B2 | 6/2011 | Rosenberg et al. |
| 8,335,557 B2 | 12/2012 | Maschke |
| 8,348,931 B2 | 1/2013 | Cooper et al. |
| 8,376,934 B2 | 2/2013 | Takahashi |
| 8,396,595 B2 | 3/2013 | Dariush |
| 8,442,618 B2 | 5/2013 | Strommer et al. |
| 8,469,945 B2 | 6/2013 | Schena |
| 8,498,691 B2 | 7/2013 | Moll et al. |
| 8,506,555 B2 | 8/2013 | Ruiz Morales |
| 8,554,368 B2 | 10/2013 | Fielding et al. |
| 8,720,448 B2 | 5/2014 | Reis et al. |
| 8,738,181 B2 | 5/2014 | Greer et al. |
| 8,827,948 B2 | 9/2014 | Romo et al. |
| 8,894,610 B2 | 11/2014 | MacNamara et al. |
| 8,929,631 B2 | 1/2015 | Pfister et al. |
| 8,945,095 B2 | 2/2015 | Blumenkranz |
| 9,014,851 B2 | 4/2015 | Wong et al. |
| 9,023,060 B2 | 5/2015 | Cooper et al. |
| 9,129,417 B2 | 9/2015 | Zheng et al. |
| 9,173,713 B2 | 11/2015 | Hart et al. |
| 9,199,372 B2 | 12/2015 | Henderson et al. |
| 9,226,796 B2 | 1/2016 | Bowling |
| 9,256,940 B2 | 2/2016 | Carelsen et al. |
| 9,259,274 B2 | 2/2016 | Prisco |
| 9,289,578 B2 | 3/2016 | Walker et al. |
| 9,302,702 B1* | 4/2016 | Schepmann ............ B62D 5/065 |
| 9,314,306 B2 | 4/2016 | Yu |
| 9,345,456 B2 | 5/2016 | Tsonton et al. |
| 9,358,682 B2 | 6/2016 | Ruiz Morales |
| 9,504,604 B2 | 11/2016 | Alvarez |
| 9,522,034 B2 | 12/2016 | Johnson |
| 9,561,083 B2 | 2/2017 | Yu et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,675,422 B2 | 6/2017 | Hourtash et al. |
| 9,713,509 B2 | 7/2017 | Schuh et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,789,608 B2 | 10/2017 | Itkowitz et al. |
| 9,839,481 B2 | 12/2017 | Blumenkranz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 2001/0000040 A1 | 3/2001 | Adams et al. |
| 2002/0035330 A1 | 3/2002 | Cline |
| 2002/0077533 A1 | 6/2002 | Bieger et al. |
| 2002/0161280 A1 | 10/2002 | Chatenever et al. |
| 2002/0173878 A1 | 11/2002 | Watanabe |
| 2003/0045778 A1 | 3/2003 | Ohline |
| 2003/0182091 A1 | 9/2003 | Kukuk |
| 2004/0257021 A1 | 12/2004 | Chang et al. |
| 2005/0043718 A1 | 2/2005 | Madhani |
| 2005/0065400 A1 | 3/2005 | Banik |
| 2005/0107917 A1 | 5/2005 | Smith et al. |
| 2005/0222554 A1 | 10/2005 | Wallace et al. |
| 2005/0234293 A1 | 10/2005 | Yamamoto |
| 2005/0256398 A1 | 11/2005 | Hastings |
| 2005/0261551 A1 | 11/2005 | Couvillon |
| 2005/0272975 A1 | 12/2005 | McWeeney et al. |
| 2006/0015096 A1 | 1/2006 | Hauck et al. |
| 2006/0041293 A1 | 2/2006 | Mehdizadeh |
| 2006/0079745 A1 | 4/2006 | Viswanathan et al. |
| 2006/0258938 A1 | 11/2006 | Hoffman |
| 2007/0013336 A1 | 1/2007 | Nowlin et al. |
| 2007/0043455 A1 | 2/2007 | Viswanathan |
| 2007/0135886 A1 | 6/2007 | Maschke |
| 2007/0142971 A1 | 6/2007 | Schena |
| 2007/0150155 A1 | 6/2007 | Kawai |
| 2007/0232856 A1 | 10/2007 | Ueno |
| 2007/0249911 A1 | 10/2007 | Simon |
| 2007/0253599 A1 | 11/2007 | White et al. |
| 2007/0287992 A1 | 12/2007 | Diolaiti |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0108870 A1 | 5/2008 | Wiita et al. |
| 2008/0123921 A1 | 5/2008 | Gielen et al. |
| 2008/0140087 A1* | 6/2008 | Barbagli ............... B25J 9/1689 606/130 |
| 2008/0159653 A1 | 7/2008 | Dunki-Jacobs et al. |
| 2008/0231221 A1 | 9/2008 | Ogawa |

(56) References Cited

U.S. PATENT DOCUMENTS

| | | |
|---|---|---|
| 2008/0249640 A1 | 10/2008 | Vittor et al. |
| 2008/0255505 A1 | 10/2008 | Carlson et al. |
| 2008/0312771 A1 | 12/2008 | Sugiura |
| 2009/0062813 A1 | 3/2009 | Prisco |
| 2009/0076534 A1 | 3/2009 | Shelton |
| 2009/0184825 A1 | 7/2009 | Anderson |
| 2009/0198298 A1 | 8/2009 | Kaiser et al. |
| 2009/0245600 A1 | 10/2009 | Hoffman |
| 2009/0256905 A1 | 10/2009 | Tashiro |
| 2009/0259099 A1 | 10/2009 | Zhou et al. |
| 2009/0287354 A1 | 11/2009 | Choi |
| 2009/0324161 A1 | 12/2009 | Prisco |
| 2010/0030061 A1 | 2/2010 | Canfield |
| 2010/0030115 A1 | 2/2010 | Fujimoto |
| 2010/0069920 A1 | 3/2010 | Naylor et al. |
| 2010/0076263 A1 | 3/2010 | Tanaka |
| 2010/0082041 A1 | 4/2010 | Prisco |
| 2010/0121138 A1 | 5/2010 | Goldenberg et al. |
| 2010/0198170 A1 | 8/2010 | Umeda et al. |
| 2010/0204713 A1 | 8/2010 | Ruiz |
| 2010/0228266 A1 | 9/2010 | Hourtash |
| 2010/0234856 A1 | 9/2010 | Stoianovici et al. |
| 2010/0256812 A1 | 10/2010 | Tsusaka et al. |
| 2011/0009880 A1 | 1/2011 | Prisco |
| 2011/0015484 A1 | 1/2011 | Alvarez et al. |
| 2011/0021926 A1 | 1/2011 | Spencer |
| 2011/0082366 A1 | 4/2011 | Scully et al. |
| 2011/0082462 A1 | 4/2011 | Suarez |
| 2011/0137122 A1 | 6/2011 | Kawai |
| 2011/0153252 A1 | 6/2011 | Govari |
| 2011/0160570 A1 | 6/2011 | Kariv |
| 2011/0196199 A1 | 8/2011 | Donhowe et al. |
| 2011/0218676 A1 | 9/2011 | Okazaki |
| 2011/0257480 A1 | 10/2011 | Takahashi |
| 2011/0258842 A1 | 10/2011 | Dukesherer et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0069167 A1 | 3/2012 | Liu et al. |
| 2012/0071752 A1 | 3/2012 | Sewell |
| 2012/0071822 A1 | 3/2012 | Romo et al. |
| 2012/0071894 A1 | 3/2012 | Tanner et al. |
| 2012/0123441 A1 | 5/2012 | Au |
| 2012/0130217 A1 | 5/2012 | Kauphusman et al. |
| 2012/0209293 A1 | 8/2012 | Carlson |
| 2012/0215094 A1 | 8/2012 | Rahimian et al. |
| 2012/0221007 A1 | 8/2012 | Batten et al. |
| 2012/0239060 A1 | 9/2012 | Orban, III |
| 2012/0253276 A1 | 10/2012 | Govari et al. |
| 2012/0283745 A1 | 11/2012 | Goldberg et al. |
| 2012/0328077 A1 | 12/2012 | Bouvier |
| 2013/0018306 A1 | 1/2013 | Ludwin |
| 2013/0085330 A1 | 4/2013 | Ramamurthy et al. |
| 2013/0090530 A1 | 4/2013 | Ramamurthy |
| 2013/0102846 A1 | 4/2013 | Sjostrom |
| 2013/0123580 A1 | 5/2013 | Peters |
| 2013/0131503 A1 | 5/2013 | Schneider et al. |
| 2013/0165854 A1 | 6/2013 | Sandhu et al. |
| 2013/0165945 A9 | 6/2013 | Roelle |
| 2013/0209208 A1 | 8/2013 | Bailey |
| 2013/0218005 A1 | 8/2013 | Desai |
| 2013/0303891 A1 | 11/2013 | Chopra |
| 2013/0325030 A1 | 12/2013 | Hourtash et al. |
| 2014/0001235 A1 | 1/2014 | Shelton, IV |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222207 A1 | 8/2014 | Bowling et al. |
| 2014/0257333 A1 | 9/2014 | Blumenkranz |
| 2014/0276933 A1* | 9/2014 | Hart .................. A61B 34/30 606/130 |
| 2014/0277333 A1 | 9/2014 | Lewis et al. |
| 2014/0296870 A1 | 10/2014 | Stern et al. |
| 2014/0309625 A1 | 10/2014 | Okamoto et al. |
| 2014/0316420 A1 | 10/2014 | Ballard et al. |
| 2014/0343569 A1 | 11/2014 | Turner |
| 2014/0357984 A1 | 12/2014 | Wallace et al. |
| 2014/0364870 A1 | 12/2014 | Alvarez et al. |
| 2015/0073267 A1 | 3/2015 | Brannan |
| 2015/0088161 A1 | 3/2015 | Hata |
| 2015/0104284 A1 | 4/2015 | Riedel |
| 2015/0119628 A1 | 4/2015 | Bharat et al. |
| 2015/0150635 A1 | 6/2015 | Kilroy |
| 2015/0150636 A1 | 6/2015 | Hagn et al. |
| 2015/0202015 A1 | 7/2015 | Elhawary |
| 2015/0223902 A1 | 8/2015 | Walker et al. |
| 2015/0265359 A1 | 9/2015 | Camarillo |
| 2015/0265807 A1 | 9/2015 | Park et al. |
| 2015/0311838 A1* | 10/2015 | Moule .................. B62D 5/0403 318/400.22 |
| 2015/0342695 A1 | 12/2015 | He |
| 2015/0359597 A1 | 12/2015 | Gombert et al. |
| 2015/0374956 A1 | 12/2015 | Bogusky |
| 2016/0000495 A1 | 1/2016 | Elliott |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0075030 A1 | 3/2016 | Takahashi |
| 2016/0081568 A1 | 3/2016 | Kolberg |
| 2016/0100772 A1 | 4/2016 | Ikuma |
| 2016/0166320 A1 | 6/2016 | Ciulla |
| 2016/0183841 A1 | 6/2016 | Duindam et al. |
| 2016/0184032 A1 | 6/2016 | Romo |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0331469 A1 | 11/2016 | Hall et al. |
| 2016/0338787 A1 | 11/2016 | Popovic |
| 2016/0346038 A1 | 12/2016 | Helgeson |
| 2016/0346924 A1 | 12/2016 | Hasegawa |
| 2016/0354057 A1 | 12/2016 | Hansen et al. |
| 2016/0360947 A1 | 12/2016 | Iida |
| 2016/0360949 A1 | 12/2016 | Hyodo |
| 2017/0007337 A1* | 1/2017 | Dan .................. A61B 34/30 |
| 2017/0056215 A1 | 3/2017 | Nagesh et al. |
| 2017/0068796 A1 | 3/2017 | Passerini et al. |
| 2017/0100197 A1 | 4/2017 | Zubiate |
| 2017/0106904 A1* | 4/2017 | Hanson .................. B62D 6/10 |
| 2017/0119481 A1 | 5/2017 | Romo et al. |
| 2017/0135718 A1 | 5/2017 | Lyons |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0231647 A1 | 8/2017 | Saunders |
| 2017/0245854 A1* | 8/2017 | Zemlok ............ A61B 17/07207 |
| 2017/0245885 A1 | 8/2017 | Lenker |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0303889 A1 | 10/2017 | Grim |
| 2017/0304015 A1 | 10/2017 | Tavallaei et al. |
| 2017/0312481 A1 | 11/2017 | Covington |
| 2017/0325715 A1 | 11/2017 | Mehendale et al. |
| 2017/0326337 A1 | 11/2017 | Romascanu |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0064498 A1 | 3/2018 | Kapadia |
| 2018/0169671 A1 | 6/2018 | Winter |

(56) References Cited

U.S. PATENT DOCUMENTS

| | | |
|---|---|---|
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289394 A1 | 10/2018 | Shah |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1 | 1/2020 | Barbagli et al. |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0101264 A1 | 4/2020 | Jiang |
| 2020/0107894 A1 | 4/2020 | Wallace |

FOREIGN PATENT DOCUMENTS

| | | | |
|---|---|---|---|
| CN | 103767659 | 5/2014 | |
| CN | 104931059 | 9/2018 | |
| DE | 102013100605 | 7/2014 | |
| EP | 1 250 986 | 10/2002 | |
| EP | 1 566 150 | 8/2005 | |
| EP | 1 800 593 | 6/2007 | |
| EP | 2 158 834 | 3/2010 | |
| EP | 2 392 435 | 12/2011 | |
| EP | 3 025 630 | 6/2016 | |
| EP | 2 615 992 | 7/2016 | |
| JP | 57073644 A * | 5/1982 | ............ B25B 23/14 |
| JP | 2008-528130 | 7/2008 | |
| JP | 2009-509654 | 3/2009 | |
| JP | 2009-524530 | 7/2009 | |
| JP | 2011-088260 | 5/2011 | |
| JP | 2013-510662 | 3/2013 | |
| RU | 2569699 C2 | 11/2015 | |
| WO | WO 01/56457 | 8/2001 | |
| WO | WO 04/029782 | 4/2004 | |
| WO | WO 05/087128 | 9/2005 | |
| WO | WO 06/122061 | 11/2006 | |
| WO | WO 09/120940 | 10/2009 | |
| WO | WO 10/127162 | 11/2010 | |
| WO | WO 11/002215 | 1/2011 | |
| WO | WO 11/132409 | 10/2011 | |
| WO | WO 12/082719 | 6/2012 | |
| WO | WO 14/114551 | 7/2014 | |
| WO | WO 15/142957 | 9/2015 | |
| WO | WO 17/048194 | 3/2017 | |
| WO | WO 17/053698 | 3/2017 | |

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.

Lawton et al., 1999, Ribbons and groups: A thin rod theory for catheters and filaments, J. Phys. A., 1999, 32:1709-1735.

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

International Search Report and Written Opinion in application No. PCT/US2019/053639, dated Jan. 27, 2020.

* cited by examiner

SYSTEMS AND METHODS FOR DOCKING MEDICAL INSTRUMENTS

PRIORITY APPLICATION(S)

This application claims priority to U.S. Provisional Patent Application No. 62/738,483, filed Sep. 28, 2018, the entirety of which is incorporated herein by reference. Any and all applications for which a foreign or domestic priority claim is identified in the Application Data Sheet as filed with the present application are hereby incorporated by reference under 37 CFR 1.57.

TECHNICAL FIELD

The systems and methods disclosed herein are directed to docking medical instruments, and more particularly, to systems and methods for docking robotic medical instruments, which may include pre-tensioned pull wires, to corresponding instrument drive mechanisms.

BACKGROUND

Robotically-enabled medical systems can be used in a wide variety of medical procedures, including endoscopy, laparoscopy, and others. In some of these procedures, a robotically controlled medical instrument can be docked to an instrument positioning device such as a robotic arm. Once docked, the instrument positioning device can manipulate the medical instrument to perform the procedure.

SUMMARY

The systems, methods and devices of this disclosure each have several innovative aspects, no single one of which is solely responsible for the desirable attributes disclosed herein.

In a first aspect, a robotic medical system includes an instrument drive mechanism comprising a drive output configured to rotate and engage a corresponding drive input on a handle of a robotic medical instrument, wherein the robotic medical instrument comprises a pre-tensioned pull wire actuated by the drive input, a motor associated with the drive output and configured to rotate the drive output, and a torque sensor associated with the drive output and configured to measure torque imparted on the drive output; and at least one computer-readable memory in communication with at least one processor, the memory having stored thereon computer-executable instructions that cause the at least one processor to activate the motor associated with the drive output to rotate the drive output in response to a torque signal from the torque sensor associated with the drive output.

In some embodiments, the robotic medical system may include one or more of the following features in any combination: (a) wherein the instructions cause the processor to rotate the drive output to align the drive output with the corresponding drive output; (b) wherein the instructions cause the processor to activate the motor in response to the torque signal exceeding a threshold; (c) wherein the instructions cause the processor to deactivate the motor in response to the torque signal dropping below the threshold; (d) wherein the torque signal is indicative of a direction of a torque imparted on the drive output, and wherein the instructions cause the processor to activate the motor to cause rotation of the motor in a direction that is the same as the direction of the imparted torque; (e) wherein a speed of rotation of the motor is proportional to a measured torque determined based on the torque signal; (f) wherein a speed of rotation of the motor is constant; (g) wherein the drive output is a gear and the drive input is a socket; (h) wherein the drive output is a socket and the drive input is a gear; (i) wherein the instructions cause the processor to activate the motor associated with the drive output to rotate the drive output in response to the torque signal when the system is in a load instrument state; (j) the torque sensor comprises a strain gauge; (k) wherein the strain gauge is positioned between a housing of the instrument drive mechanism and the motor; and/or (l) wherein the torque sensor is bi-directional.

In another aspect, a computer readable medium can include instructions configured to cause at least one processor to receive a torque signal from a torque sensor associated with a drive output of an instrument drive mechanism; activate a motor associated with the drive output to rotate the drive output in response to the torque signal from the torque sensor exceeding a threshold; and deactivate the motor to cause the motor to stop rotating the drive output in response to the torque signal from the torque sensor dropping below the threshold.

In some embodiments, the computer readable medium may further include one or more of the following features in any combination: (a) wherein the instructions are configured to cause at least one processor to rotate the drive output to align the drive output with a drive input or a robotic medical instrument, wherein the robotic medical instrument comprises at least one pre-tensioned pull wire associated with the drive input; (b) wherein the torque signal is indicative of a direction of a torque imparted on the drive output, and wherein the instructions cause the at least one processor to activate the motor to cause rotation of the motor in a direction that is the same as the direction of the imparted torque; (c) wherein the instructions are configured to cause the motor to rotate the drive output at a speed of rotation that is proportional to a measured torque determined based on the torque signal; (d) wherein the instructions are configured to cause the motor to rotate the drive output at a speed of rotation that is constant; and/or (e) wherein the instructions cause the at least one processor to activate the motor associated with the drive output to rotate the drive output in response to the torque signal when the system is in a load instrument state.

In another aspect, a method for aligning a drive output of an instrument drive mechanism with a drive input of a robotic medical instrument includes receiving a torque signal from a torque sensor associated with the drive output of the instrument drive mechanism, the torque signal indicative of a torque imparted on the drive output; comparing the torque signal to a threshold; activating a motor of the instrument drive mechanism associated with the drive output to cause rotation of the drive output in response to the torque signal exceeding the threshold; and deactivating the motor to cause the motor to stop rotating the drive output in response to the torque signal from the torque sensor dropping below the threshold.

In some embodiments, the method can include one or more of the following features in any combination: (a) wherein the drive output is rotated to align the drive output with the drive input of the robotic medical instrument; (b) wherein the robotic medical instrument comprises at least one pre-tensioned pull wire associated with the drive input; (c), wherein the torque signal is indicative of a direction of a torque imparted on the drive output, and wherein the method comprises activating the motor to cause rotation of the motor in a direction that is the same as the direction of the imparted torque; (d) wherein a speed of rotation of the motor is proportional to a measured torque determined based on the torque signal; (e) wherein a speed of rotation of the motor is constant; (f) wherein the drive output is a gear and the drive input is a socket; (g) wherein the drive output is a socket and the drive input is a gear; and/or (h) wherein the activating and deactivating steps occur when in a load instrument state.

In another aspect, a robotic medical system includes an instrument drive mechanism comprising a drive output configured to rotate and engage a drive input on a handle of a robotic medical instrument, wherein the robotic medical instrument comprises a pull wire associated with the drive input, a motor associated with the drive output and configured to rotate the drive output, and a torque sensor associated with the drive output and configured to measure torque imparted on the drive output; and at least one computer-readable memory in communication with at least one processor, the memory having stored thereon computer-executable instructions that cause the at least one processor to: activate the motor associated with the drive output to rotate the drive output in a first direction until a first rotational position at which a torque signal measured by the torque sensor associated with the drive output exceeds a threshold, cause the motor to rotate the drive output in a second direction until a second rotational position at which the torque signal measured by the torque sensor exceeds the threshold, and determine a rotational distance between the first rotational position and the second rotational position.

In some embodiments, the system may include one or more of the following features in any combination: (a) wherein the rotational distance is indicative of a gap between the drive output and the drive input; (b) wherein the torque signal exceeding the threshold is indicative of the drive output contacting the drive input; (c) wherein the instructions cause the at least one processor to rotate the drive output to articulate an elongated shaft of the medical instrument, and wherein the rotation is based at least in part of the determined rotational distance; (d) wherein the drive output is a gear and the drive input is a socket; (e) wherein the drive output is a socket and the drive input is a gear; (f) wherein the instructions cause the processor to activate the motor associated with the drive output to rotate the drive output to align the drive output with the drive input in response to the torque signal when the system is in a homing state; (g) wherein the system enters the homing state after the medical instrument is docked to the instrument drive mechanism; (h) wherein the torque sensor comprises a strain gauge; (i) wherein the strain gauge is positioned between a housing of the instrument drive mechanism and the motor; and/or (j) wherein the torque sensor is bi-directional.

In another aspect, a computer readable medium includes instructions configured to cause at least one processor to: activate a motor associated with a drive output of an instrument drive mechanism to rotate the drive output in a first direction until a first rotational position at which a torque signal measured by a torque sensor associated with the drive output exceeds a threshold; cause the motor to rotate the drive output in a second direction until a second rotational position at which the torque signal measured by the torque sensor exceeds the threshold; and determine a rotational distance between the first rotational position and the second rotational position.

In some embodiments, the computer readable instructions may further include one or more of the following features in any combination: (a) wherein the rotational distance is indicative of a gap between the drive output and a drive input of a robotic medical instrument docked to the instrument drive mechanism; (b) wherein the torque signal exceeding the threshold is indicative of the drive output contacting the drive input; (c) wherein the instructions cause the at least one processor to rotate the drive output to articulate an elongated shaft of the medical instrument, and wherein the rotation is based at least in part of the determined rotational distance; (d) wherein the instructions cause the at least one processor to activate the motor associated with the drive output to rotate the drive output to align the drive output with the drive input in response to the torque signal when the system is in a homing state; and/or (e) wherein the system enters the homing state after the medical instrument is docked to the instrument drive mechanism.

In another aspect, a method includes: activating a motor associated with a drive output of an instrument drive mechanism to rotate the drive output in a first direction until a first rotational position at which a torque signal measured by a torque sensor associated with the drive output exceeds a threshold, causing the motor to rotate the drive output in a second direction until a second rotational position at which the torque signal measured by the torque sensor exceeds the threshold, and determining a rotational distance between the first rotational position and the second rotational position.

The method may include one or more of the following features in any combination: (a) wherein the rotational distance is indicative of a gap between the drive output and a drive input of a robotic medical instrument docked to the instrument drive mechanism; (b) wherein the torque signal exceeding the threshold is indicative of the drive output contacting the drive input; and/or (c) rotating the drive output to articulate an elongated shaft of the medical instrument, and wherein the rotation is based at least in part of the determined rotational distance.

In another aspect, a robotic medical system, includes an instrument drive mechanism comprising a drive output configured to rotate and engage a corresponding drive input on a handle of a robotic medical instrument, wherein the robotic medical instrument comprises a pre-tensioned pull wire actuated by the drive input, a motor associated with the drive output and configured to rotate the drive output, and a sensor configured to detect when the handle of the robotic medical instrument is within a threshold loading distance from the instrument drive mechanism. The system also includes at least one computer-readable memory in communication with at least one processor, the memory having stored thereon computer-executable instructions that cause the at least one processor to determine that the robotic medical instrument is within the threshold loading distance of the instrument drive mechanism based on an output of the sensor, and activate the motor associated with the drive output to cause the drive output to oscillate to facilitate alignment of the drive output and the corresponding drive input.

The system can include one or more of the following features in any combination: (a) wherein the instructions further configure the processor to place the motor in an admittance mode the robotic medical instrument is within the threshold loading distance of the instrument drive mechanism; (b) wherein the sensor is a proximity sensor; (c) wherein the sensor is a magnetic sensor; (d) wherein the sensor is an RFID reader; (e) wherein oscillation of the drive output comprises rotation of the drive output back and forth in clockwise and counter clockwise directions through a rotational range of at least 30 degrees, at least 20 degrees, at least 15 degrees, at least 10 degrees, at least 5 degrees, at least 3 degrees, or at least 1 degree; (f) wherein oscillation of the drive output comprises rotation of the drive output back and forth in clockwise and counter clockwise directions through a rotational range of no more than 30 degrees, no more than 20 degrees, no more than 15 degrees, no more than 10 degrees, no more than 5 degrees, no more than 3 degrees, or no more than 1 degree; (g) wherein the instructions further configure the processor to determine that the robotic medical instrument has docked to the instrument drive mechanism based on an output of the sensor; and stop causing oscillation of the drive output when the robotic medical instrument has docked; (h) wherein the threshold loading distance is at least 20 cm, at least 15 cm, at least 10 cm, at least 5 cm, or at least 1 cm; and/or (i) wherein the threshold loading distance is no more than 20 cm, no more than 15 cm, no more than 10 cm, no more than 5 cm, or no more than 1 cm.

In another aspect, a method includes determining that a robotic medical instrument is within a threshold loading distance of an instrument drive mechanism based on an output of a sensor on the instrument drive mechanism, and activating a motor associated with a drive output of the instrument drive mechanism to cause the drive output to oscillate to facilitate alignment of the drive output and the corresponding drive input when the robotic medical instrument is within the threshold loading distance of the instrument drive mechanism.

The method can include one or more of the following features in any combination: (a) placing the motor in an admittance mode the robotic medical instrument is within the threshold loading distance of the instrument drive mechanism; (b) wherein the sensor is a proximity sensor; (c) wherein the sensor is a magnetic sensor; (d) wherein the sensor is an RFID reader; (e) wherein oscillation of the drive output comprises rotation of the drive output back and forth in clockwise and counter clockwise directions through a rotational range of at least 30 degrees, at least 20 degrees, at least 15 degrees, at least 10 degrees, at least 5 degrees, at least 3 degrees, or at least 1 degree; (f) wherein oscillation of the drive output comprises rotation of the drive output back and forth in clockwise and counter clockwise directions through a rotational range of no more than 70 degrees, no more than 20 degrees, no more than 15 degrees, no more than 10 degrees, no more than 5 degrees, no more than 3 degrees, or no more than 1 degree; (g) determining that the robotic medical instrument has docked to the instrument drive mechanism based on an output of the sensor, and stopping oscillation of the drive output when the robotic medical instrument has docked; (h) wherein the threshold loading distance is at least 20 cm, at least 15 cm, at least 10 cm, at least 5 cm, or at least 1 cm; and/or (i) wherein the threshold loading distance is no more than 20 cm, no more than 15 cm, no more than 10 cm, no more than 5 cm, or no more than 1 cm.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 25A illustrates the drive output and the drive input in a first misaligned position. FIG. 25B illustrates the drive output and the drive input in a second misaligned position. FIG. 25C illustrates the drive input and the drive output in an aligned position. FIG. 25D illustrates an example graph of the output of a torque sensor associated with the drive output during the alignment process illustrated in FIGS. 25A-25C.

FIG. 28A illustrates the drive output engaged with the drive input. FIG. 28B illustrates the drive output rotated in a first direction to a first rotational position. FIG. 28C illustrates the drive output rotated in second direction to a second rotational position. FIG. 28D illustrates a graph of the output of a torque sensor associated with the drive output during the homing process illustrated in FIGS. 28A-28C.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
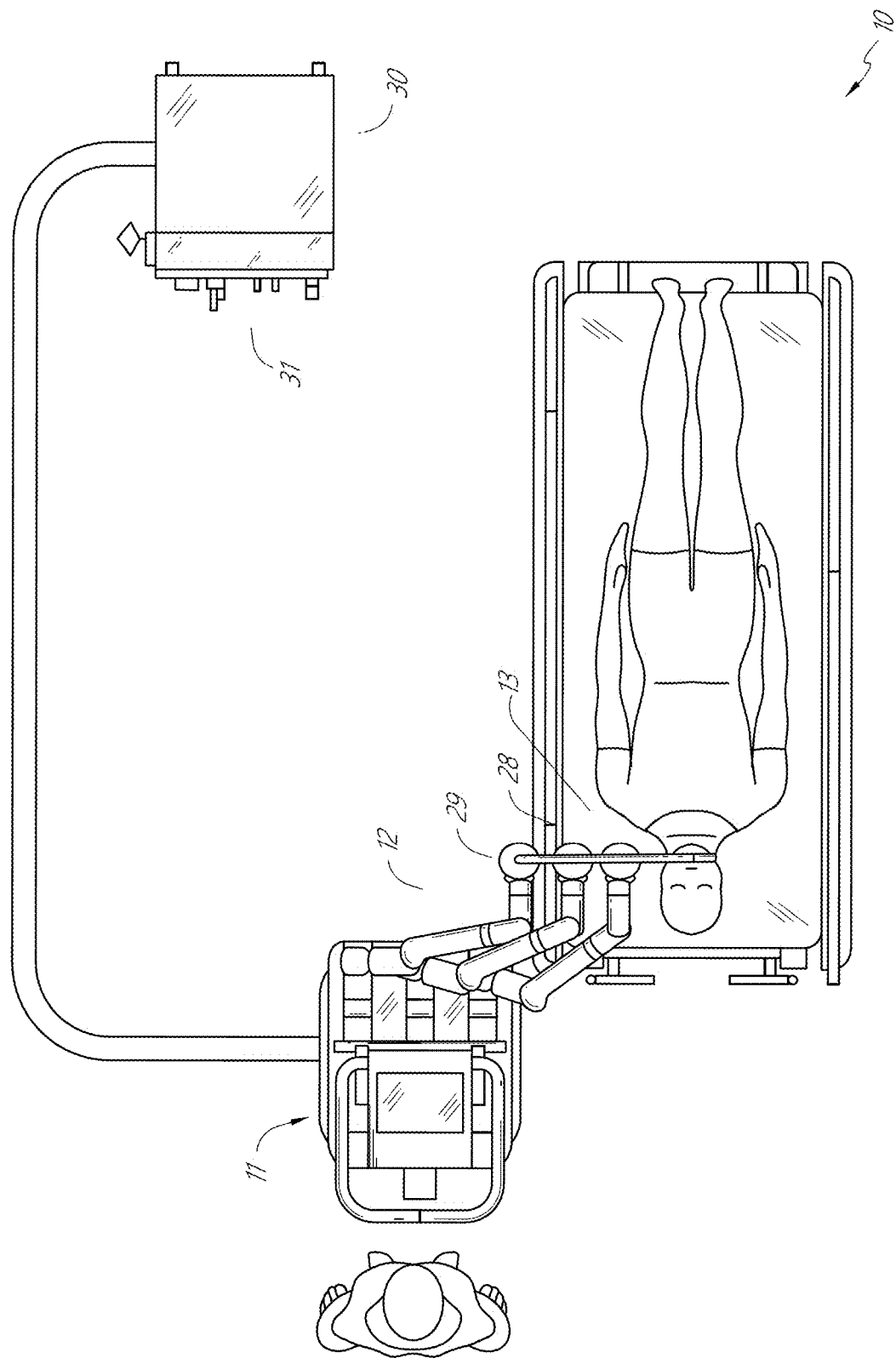
FIG. 1 illustrates an embodiment of a cart-based robotic system arranged for diagnostic and/or therapeutic bronchoscopy.
Figure 2:
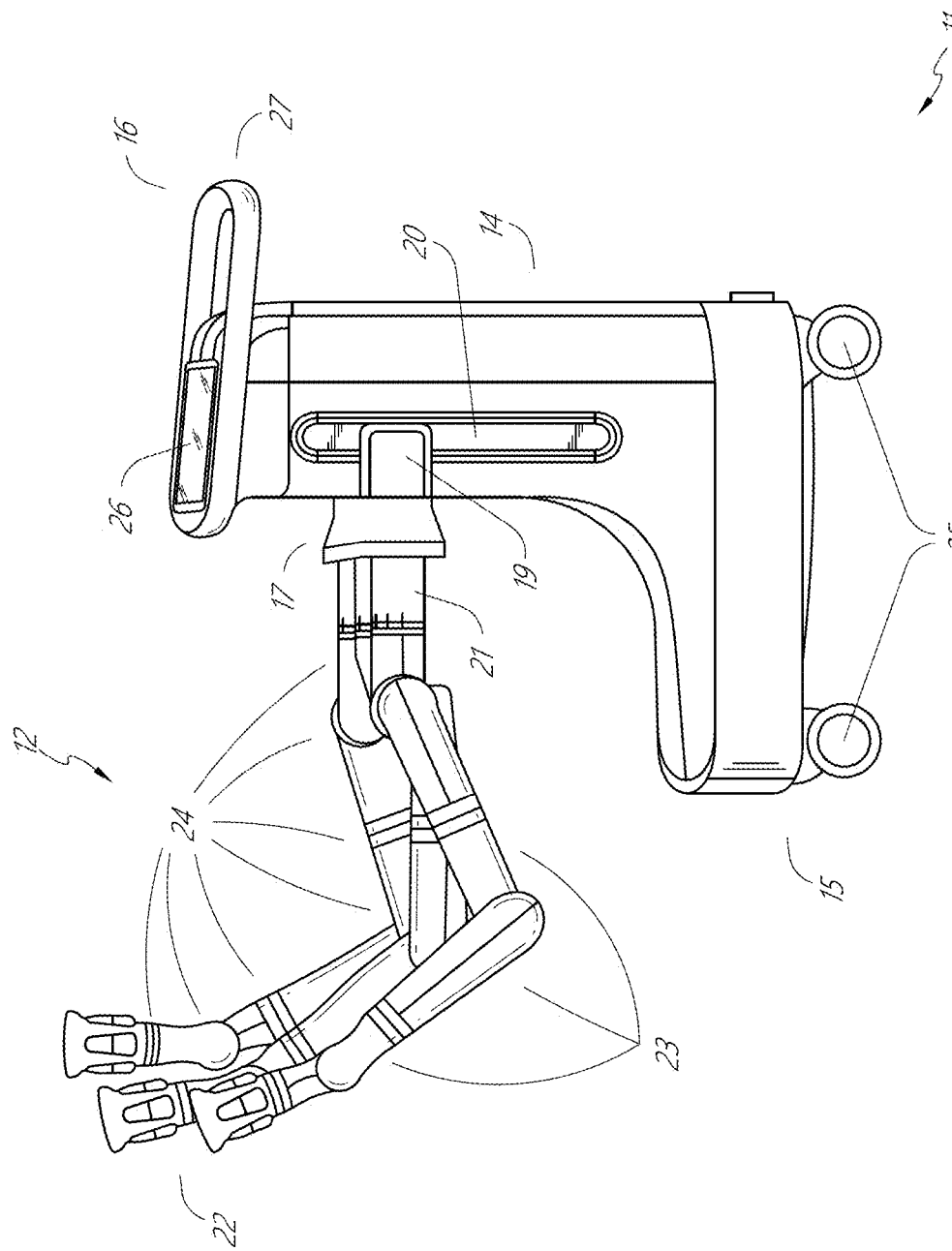
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown).

In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant"

degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include pre-operative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
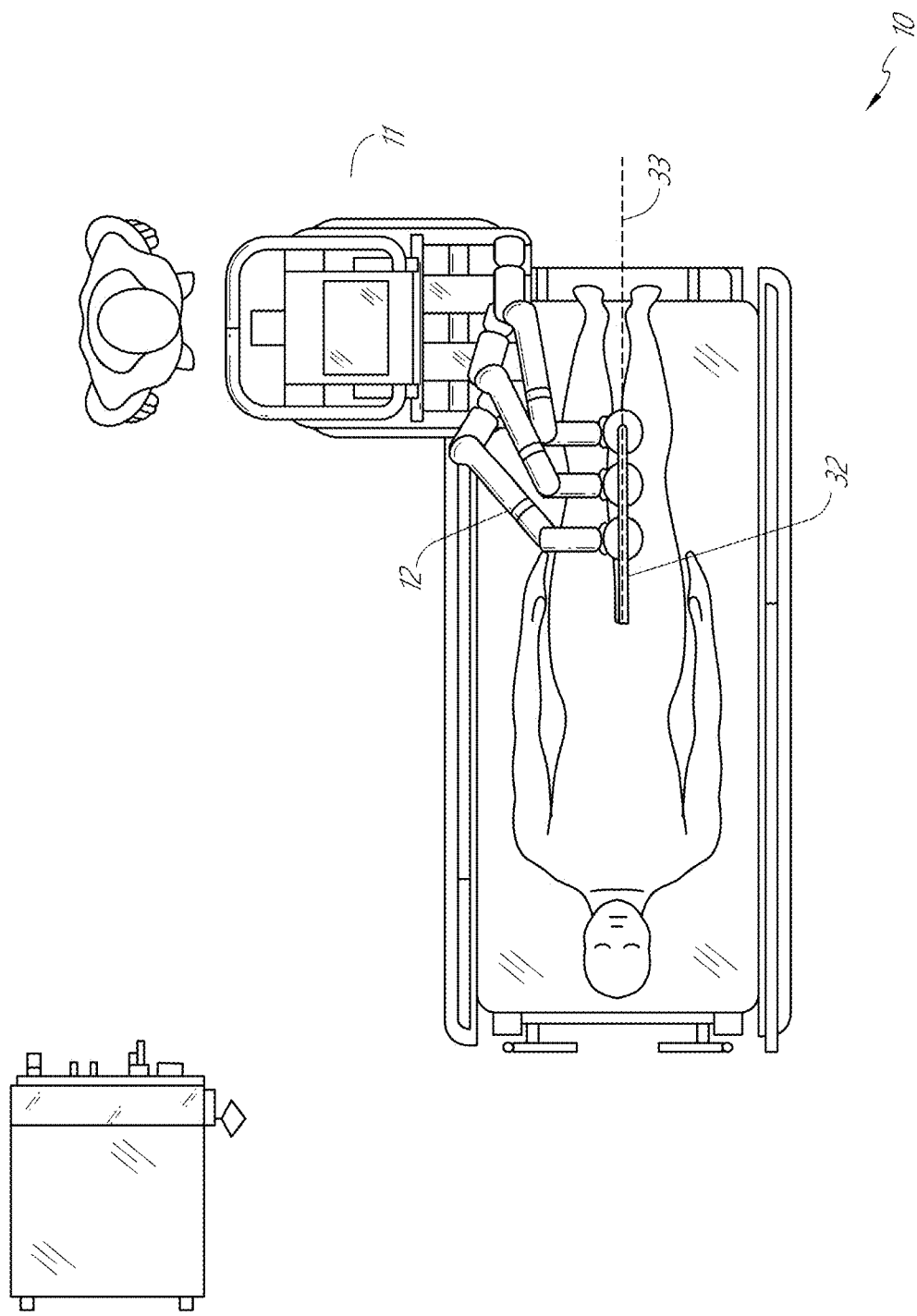
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
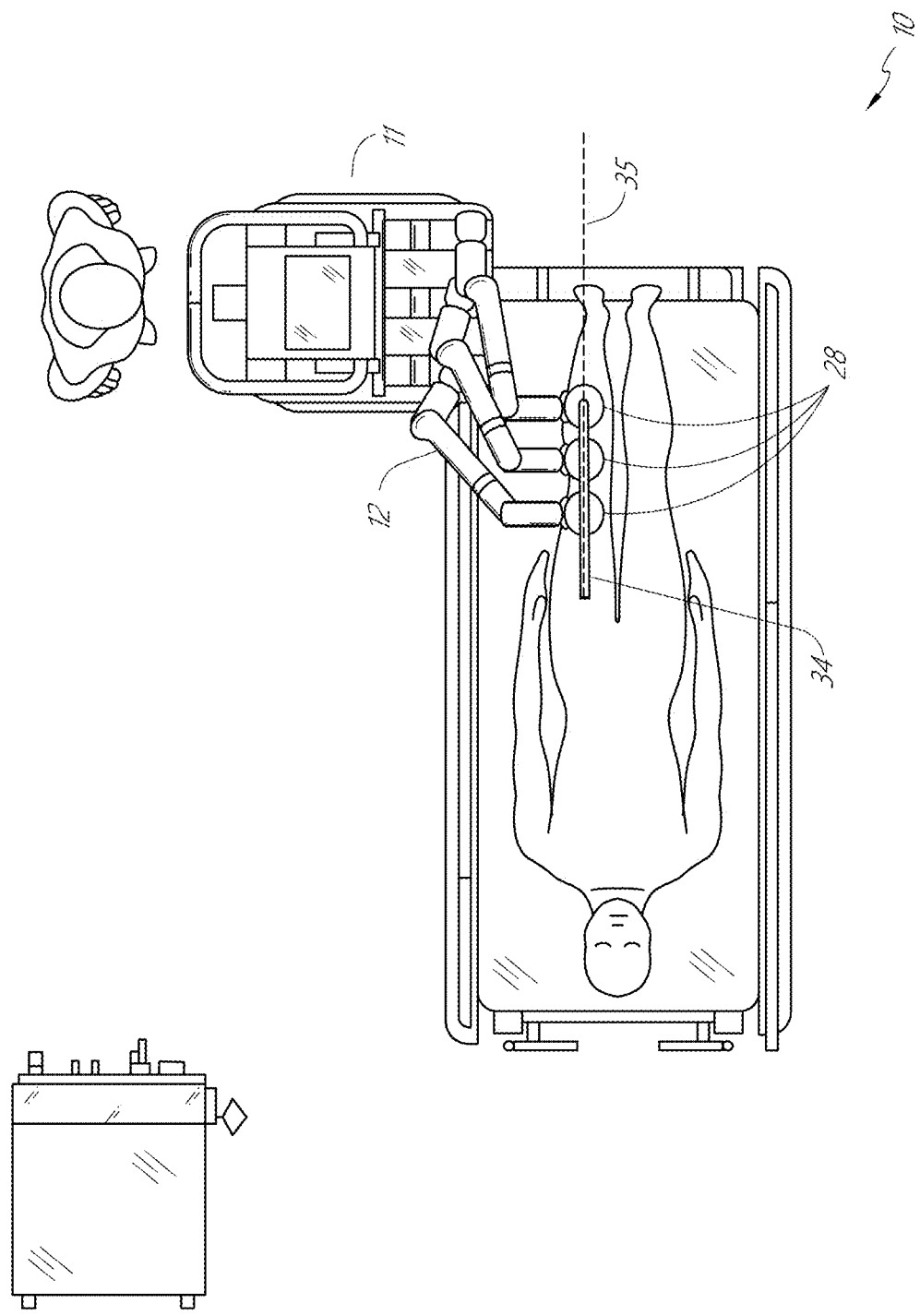
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
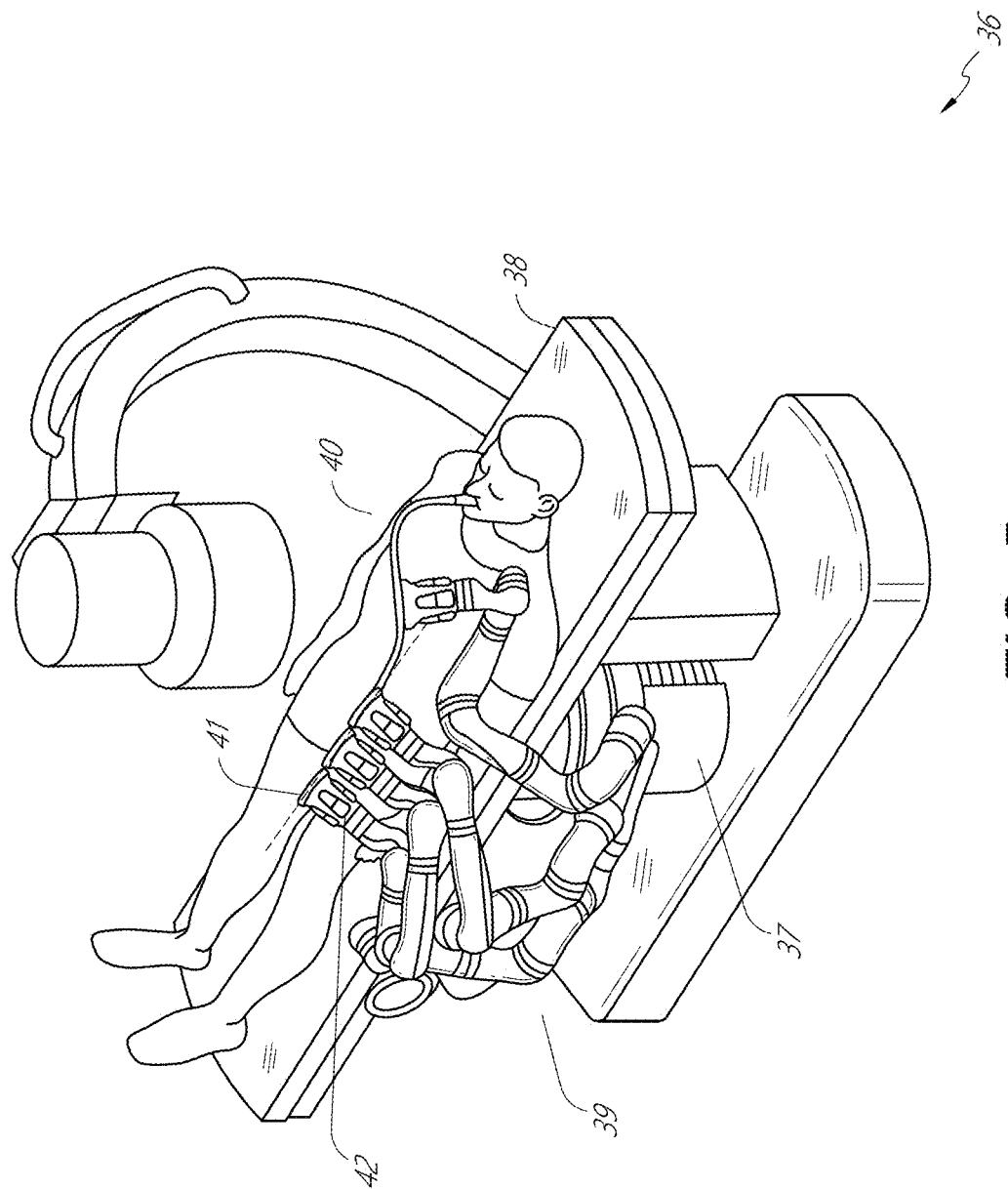
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
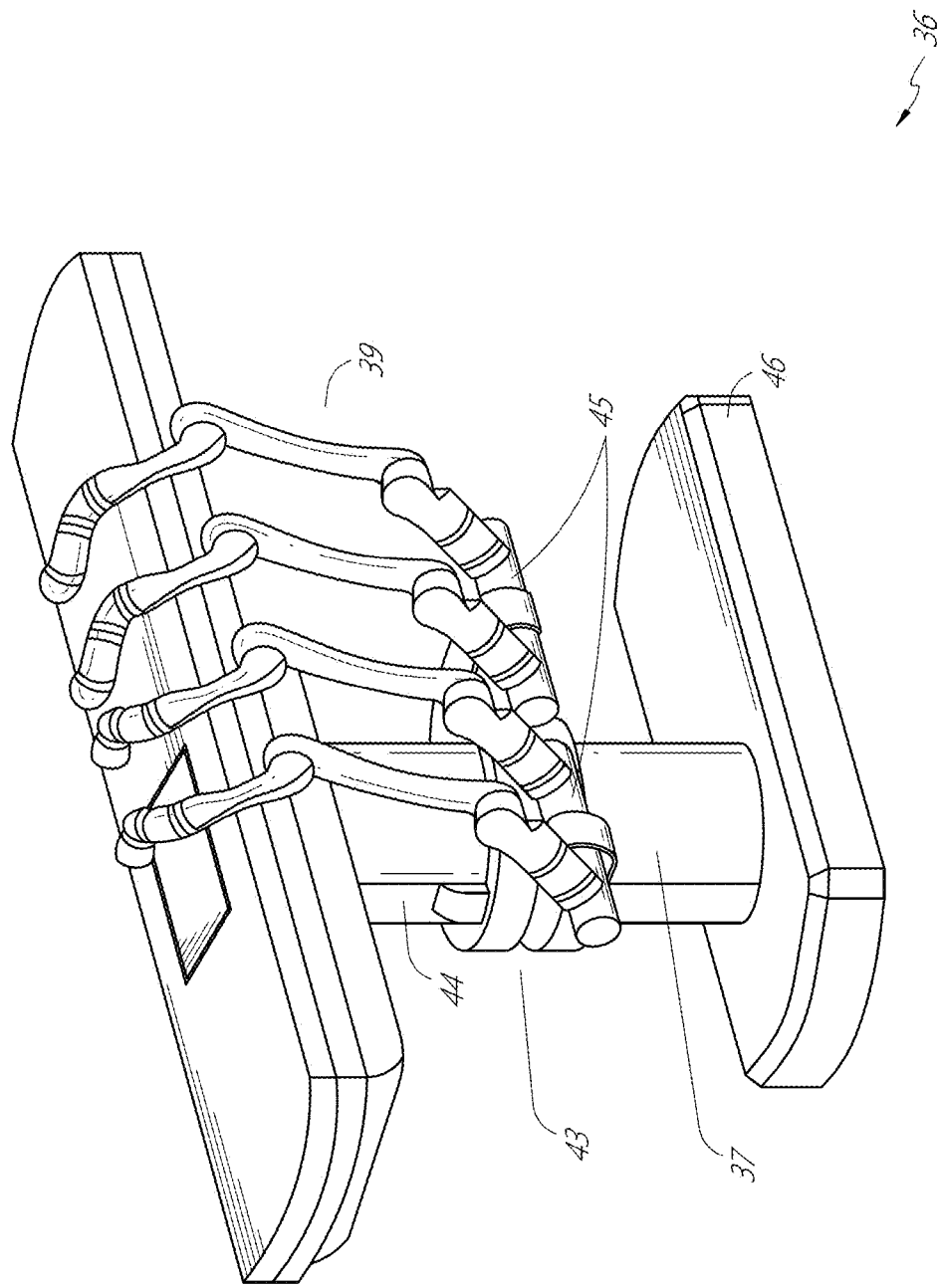
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
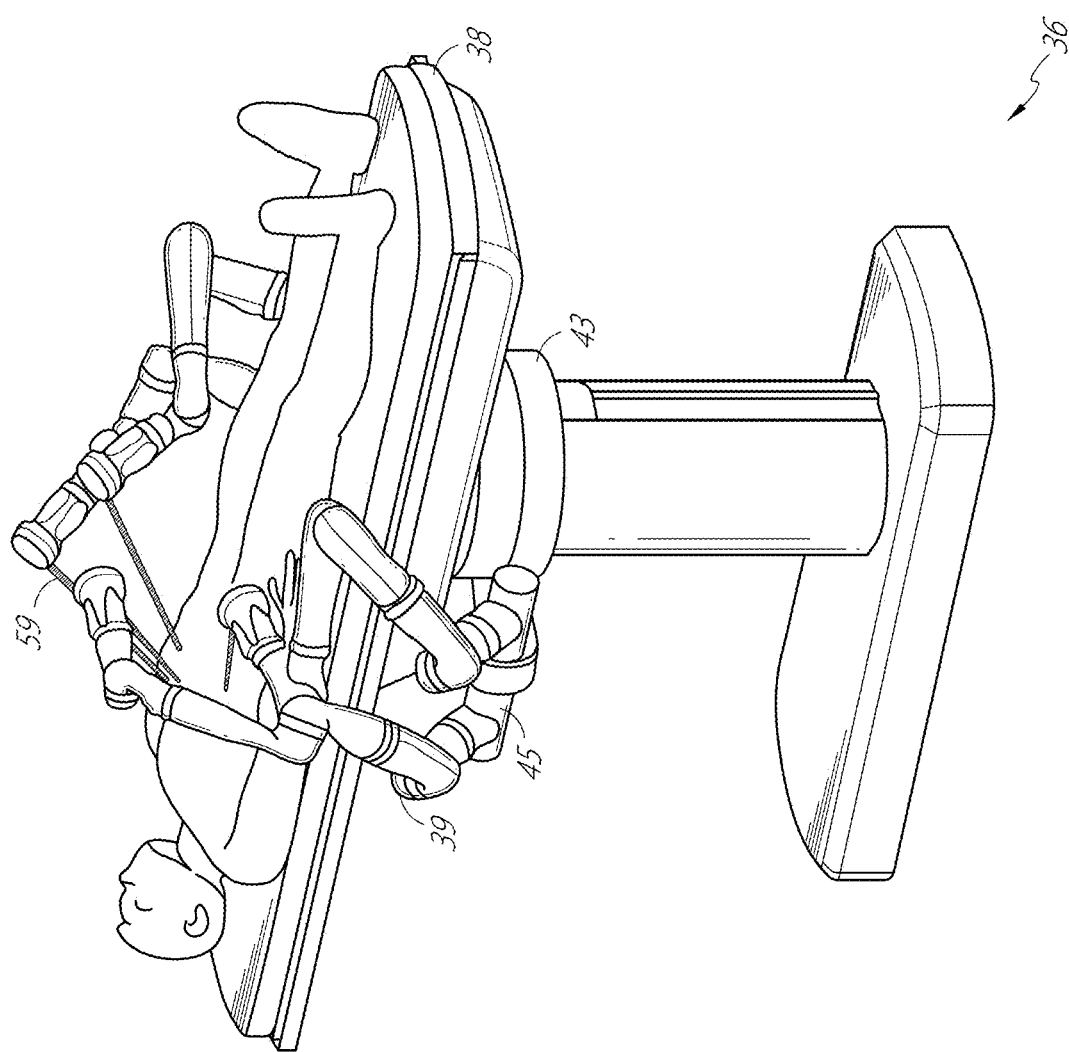
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
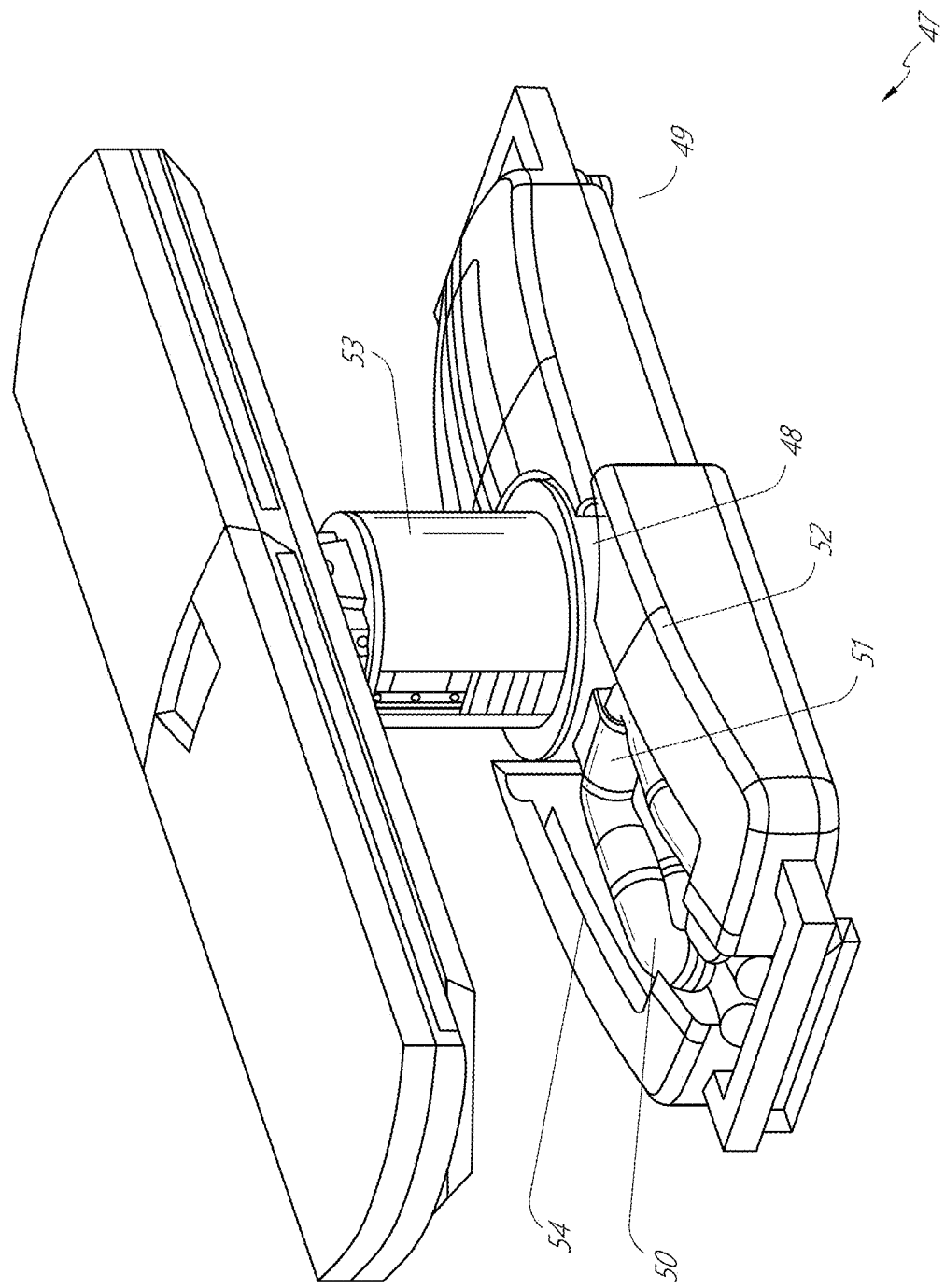
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
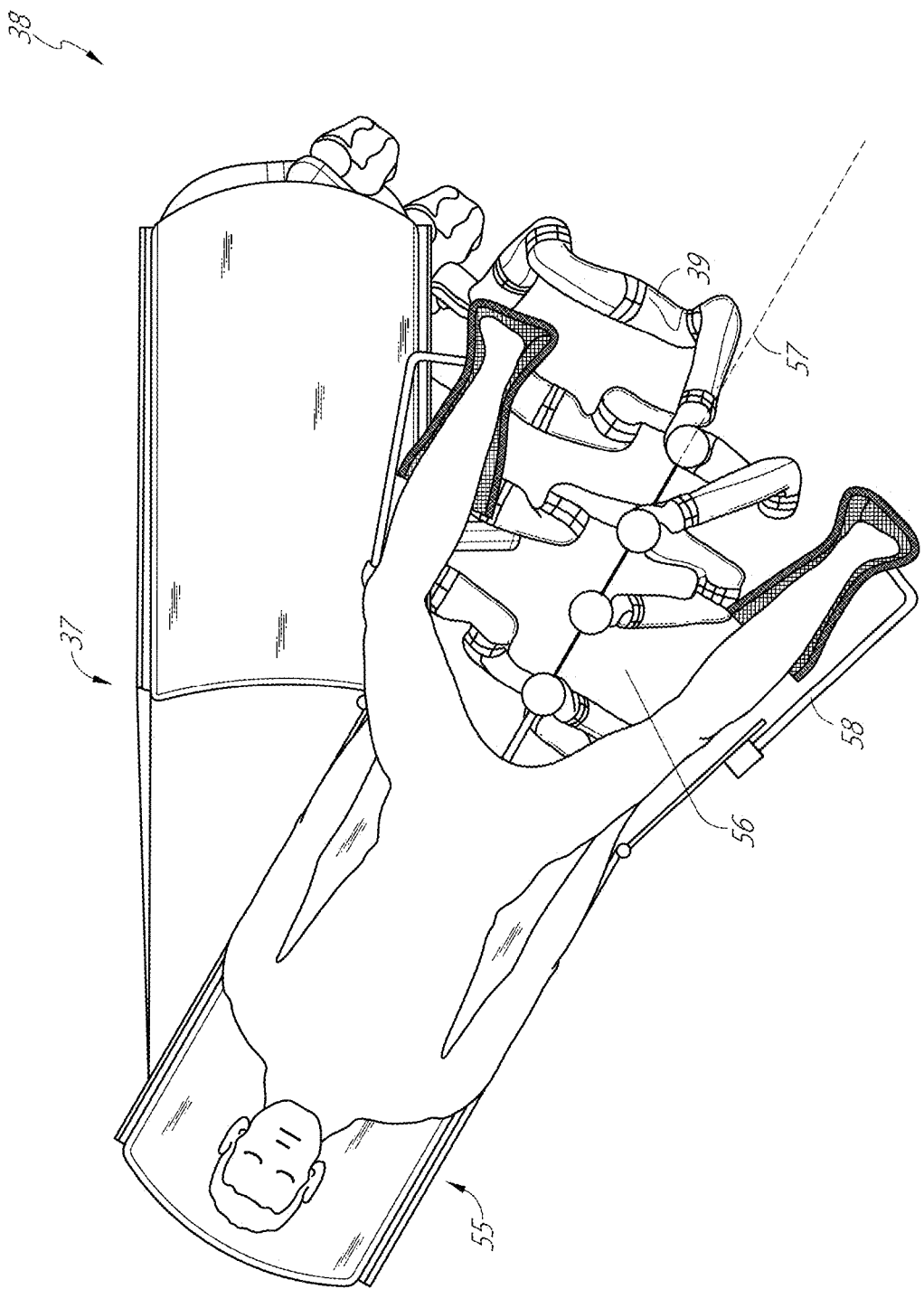
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
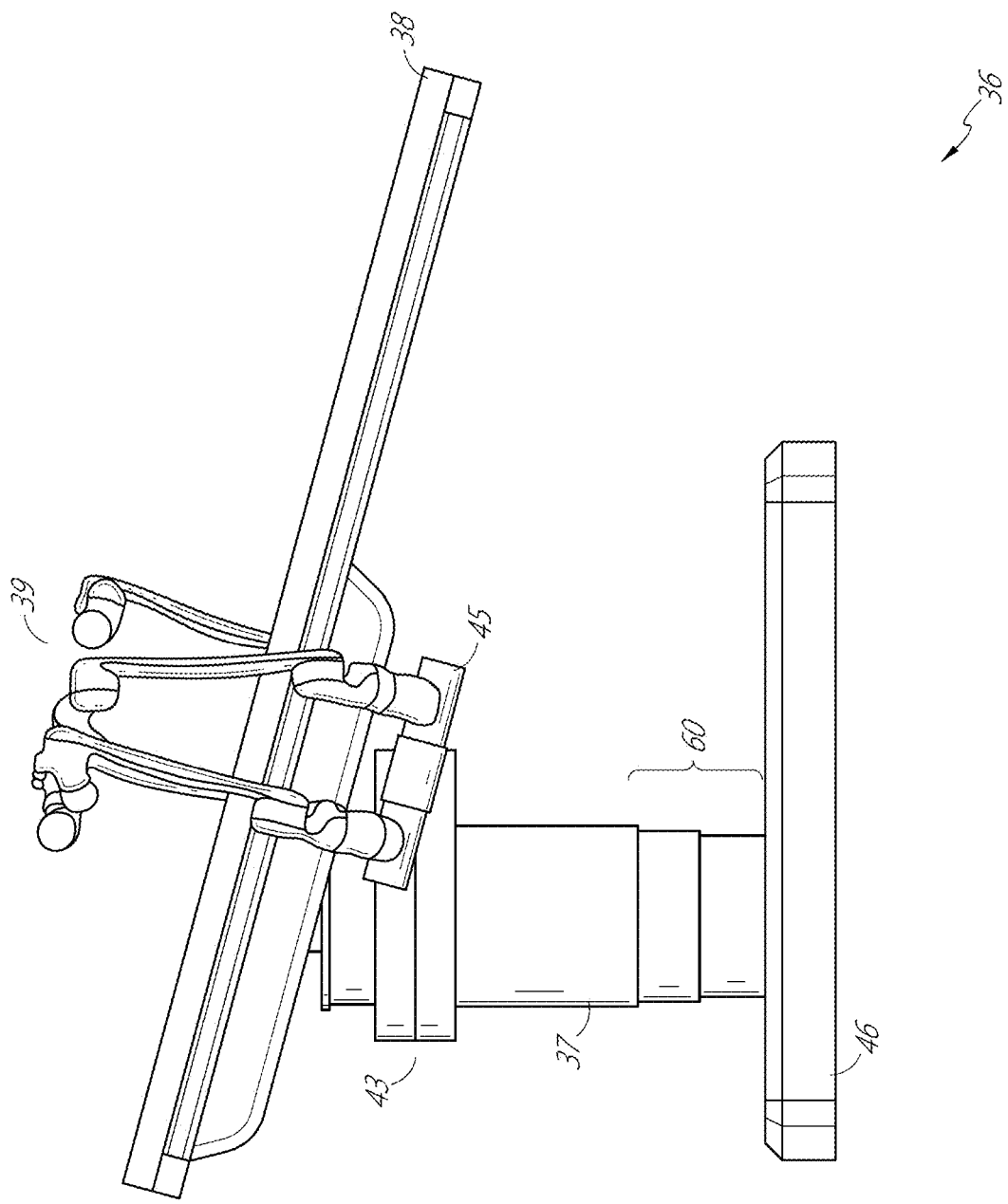
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
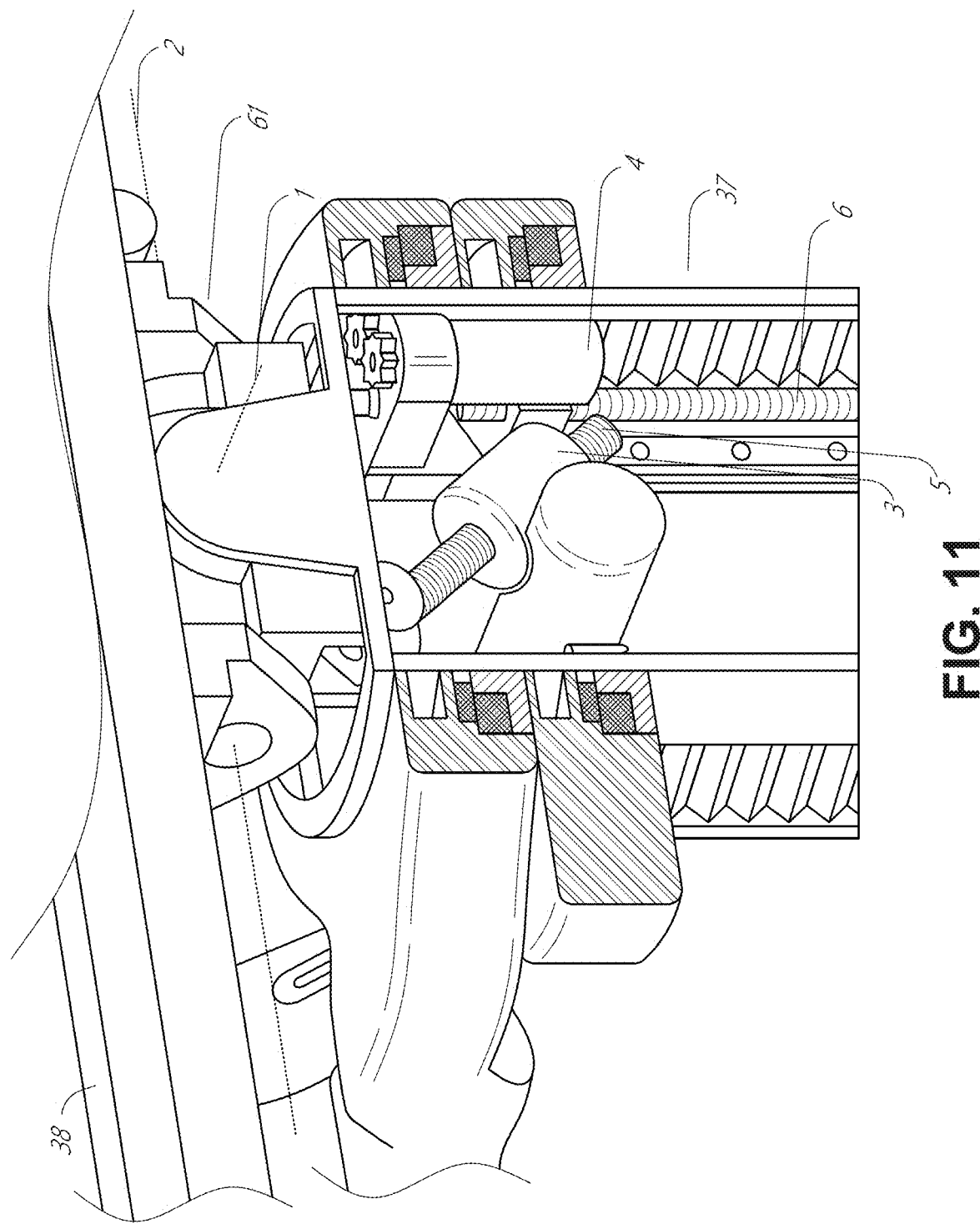
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
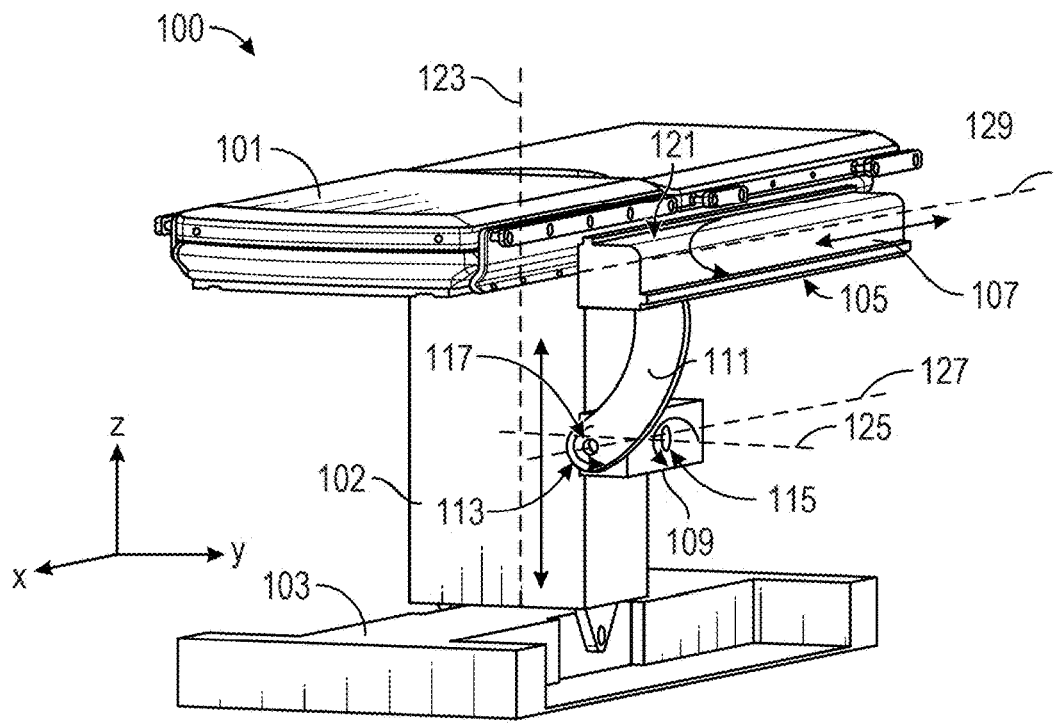
FIG. 12 illustrates an alternative embodiment of a table-based robotic system.
Figure 13:
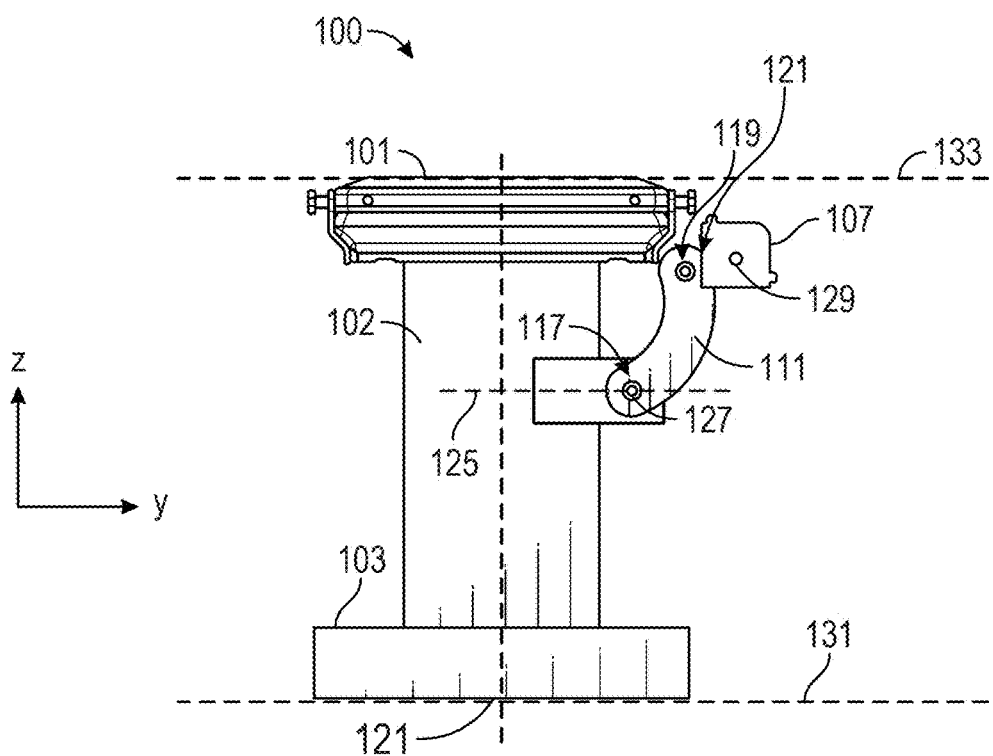
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
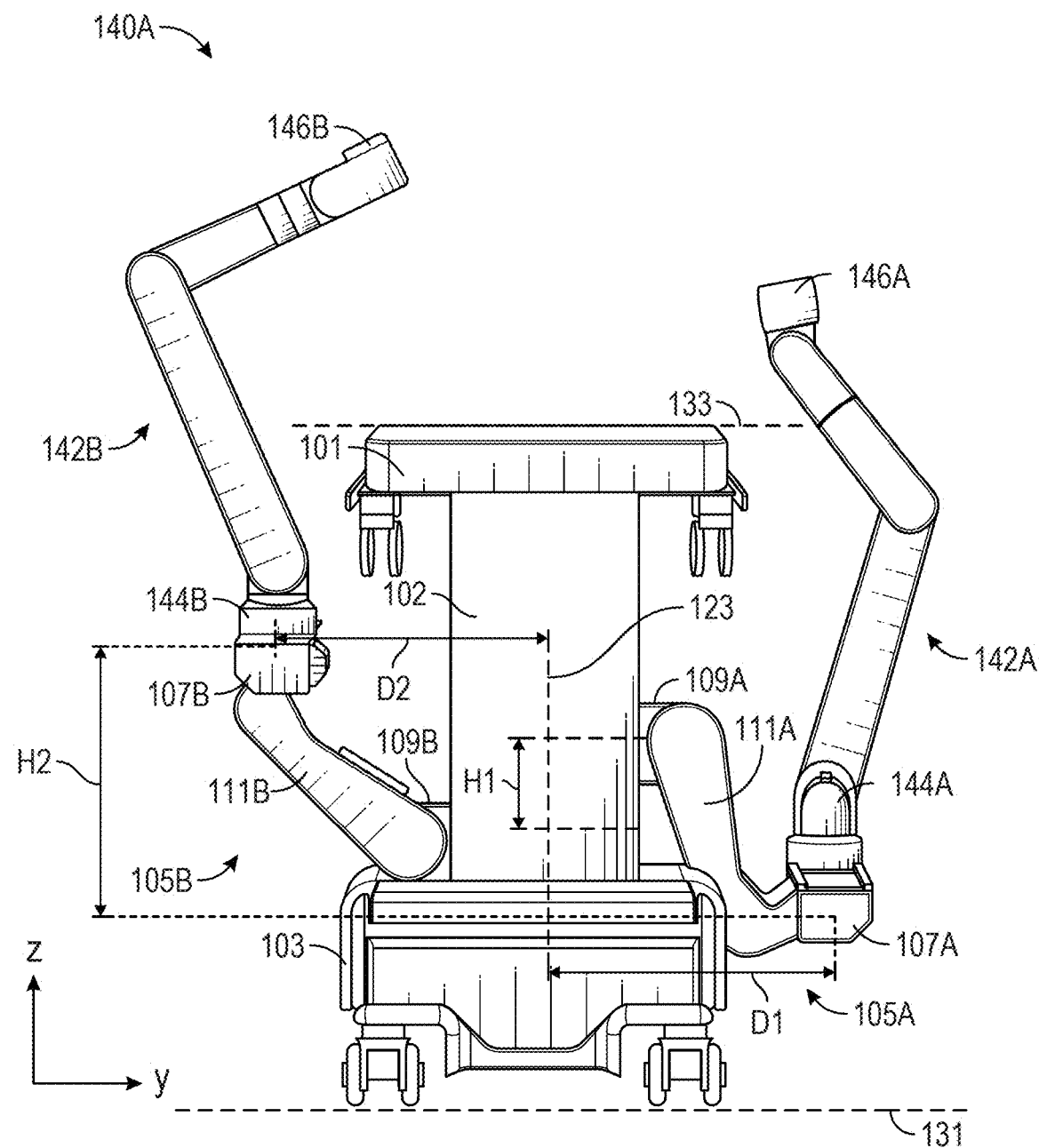
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
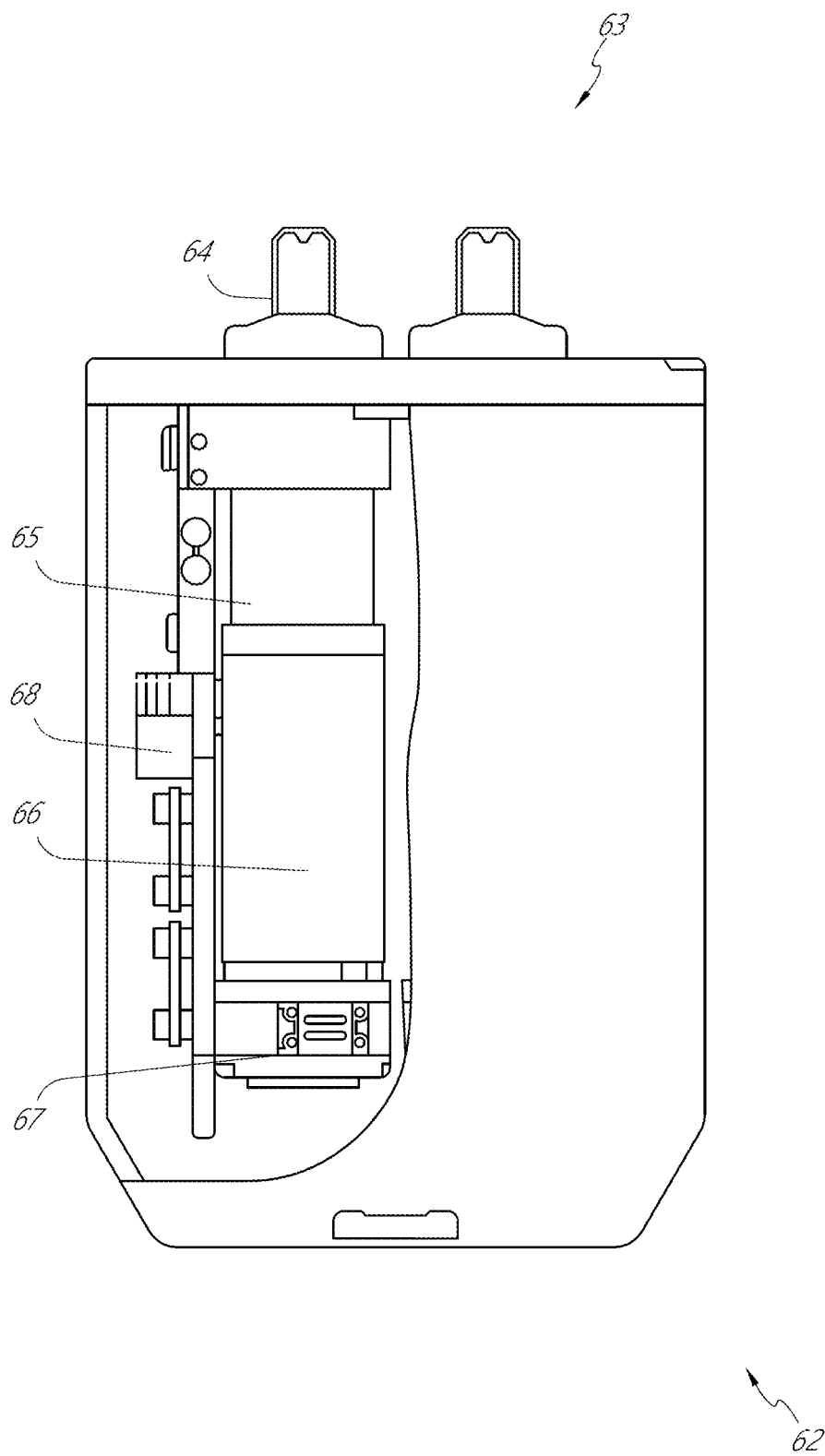
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
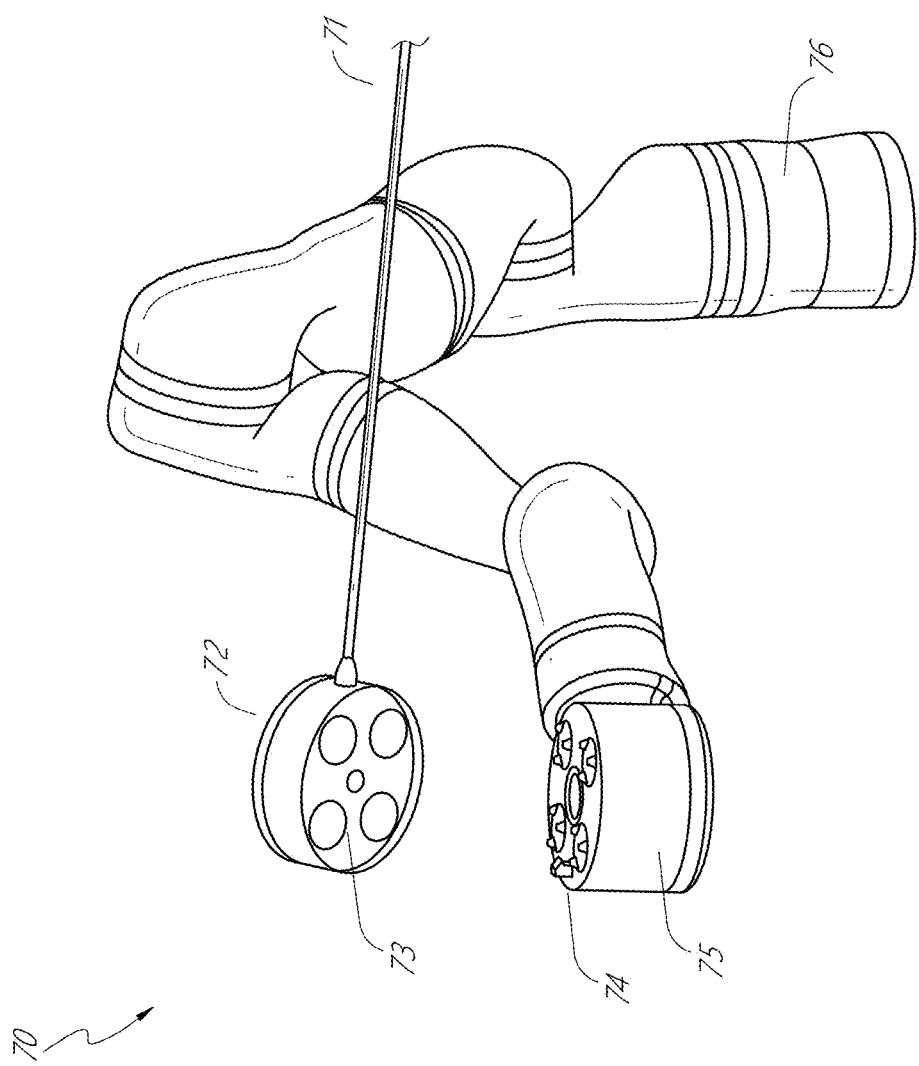
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
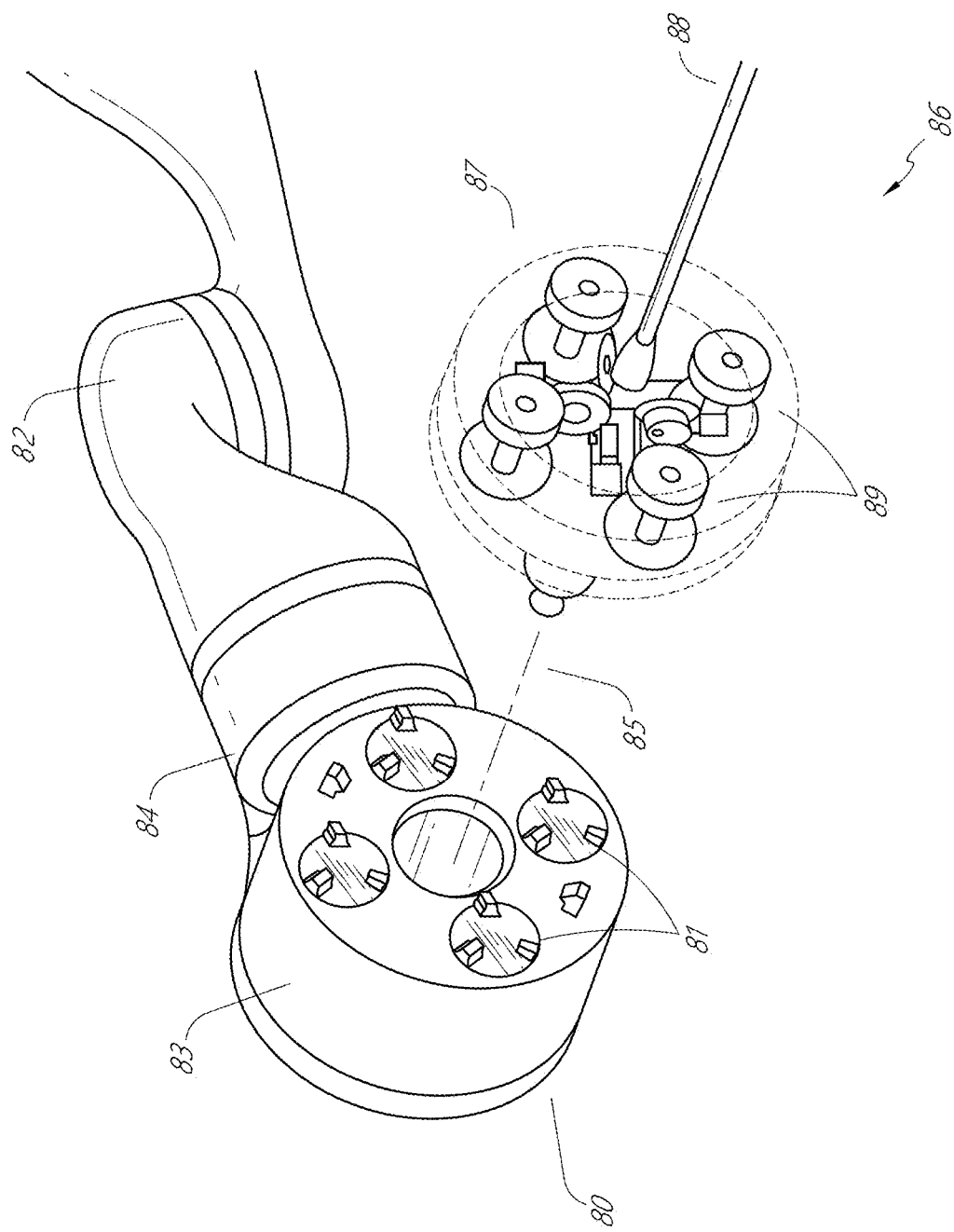
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
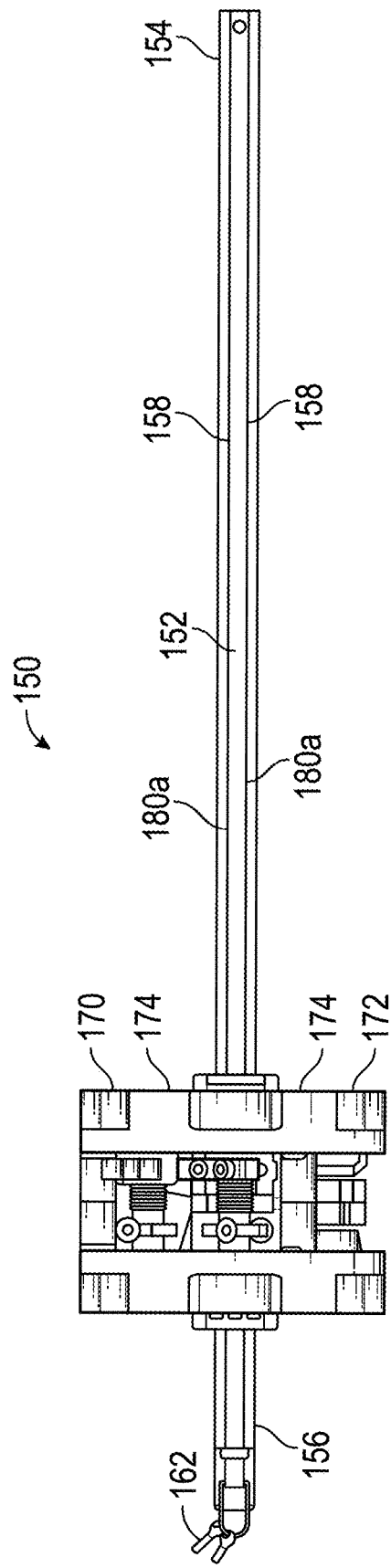
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver. In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
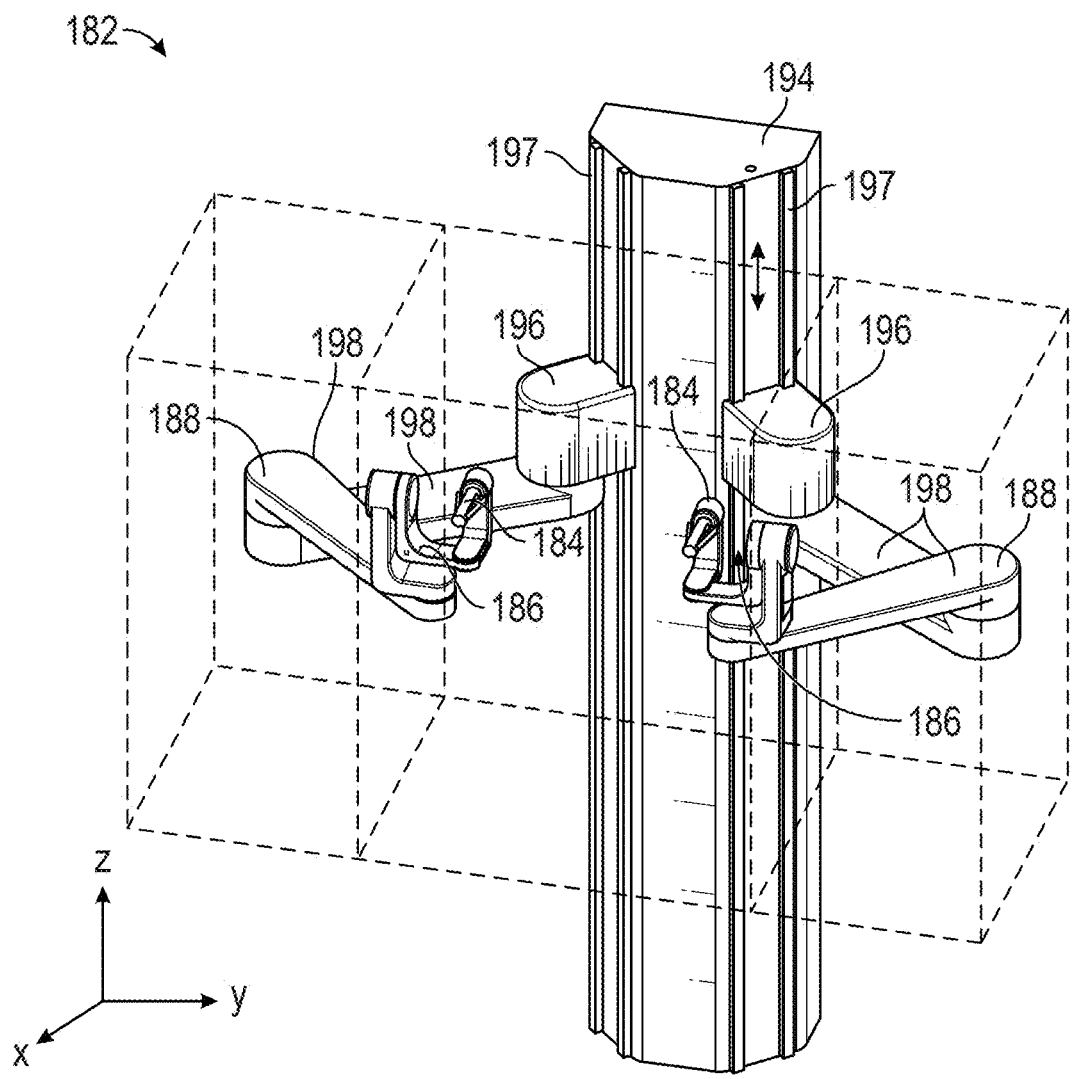
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
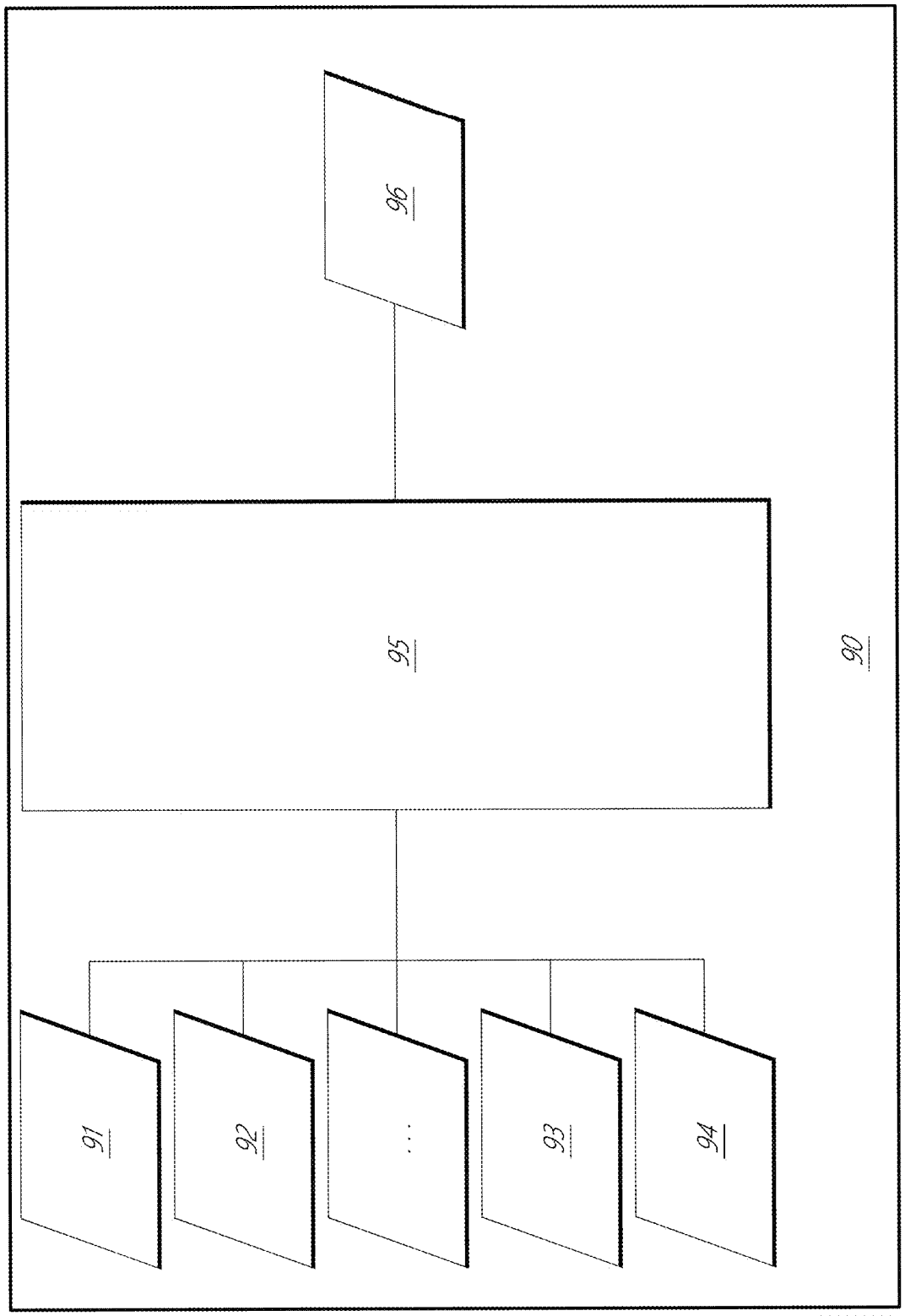
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Docking Medical Instruments.

Embodiments of the disclosure relate to systems and techniques for docking medical instruments. Some robotically controllable medical instruments include a base or handle that can be docked with an additional component of a robotic medical system. As an example, a robotically controllable endoscope can include a base or handle that is configured to be docked with an instrument drive mechanism (IDM) on a robotic arm. The instrument drive mechanism can include drive outputs that engage with corresponding drive inputs of the medical instrument to facilitate and enable control of the medical instrument. In some embodiments, the systems and techniques disclosed herein are configured to facilitate alignment between the drive outputs of the instrument drive mechanism and the drive inputs of the medical instrument. Aligning the drive outputs with the drive inputs can facilitate docking the medical instrument to the instrument drive mechanism. For example, aligning the drive outputs and drive inputs can make docking the medical instrument to the instrument drive mechanism quicker and easier. The systems and techniques described herein can be employed, for example, with robotically-enabled medical systems, such as those discussed above with reference to FIGS. 1-20, as well as those discussed below and other robotic systems. Example medical instruments and instrument drive mechanisms are described above, for example, with reference to FIGS. 15-18, as well as below.

As shown in FIG. 16, during a robotic medical procedure, a medical instrument 70 can be docked to an instrument drive mechanism 75, which can be positioned on a robotic arm 76. The medical instrument 70 can include an instrument base or handle 72 that is configured to engage with the instrument drive mechanism 75. As shown, the instrument handle 72 can include a plurality of drive inputs 73 that are configured to engage corresponding drive outputs 74 on the instrument drive mechanism 75. Detailed example embodiments of drive inputs and drive outputs are shown in FIGS. 21A-23, which are described below. As discussed above, the drive outputs 74 can be driven by motors within the instrument drive mechanism 75 (see FIG. 15). The drive outputs 74 can transfer the rotation (or other motion) of the motor to the drive inputs 75 to control various functions of the medical instrument 70, such as articulation of the elongated shaft 71 of the medical instrument 70 or actuation of a tool positioned at the distal end of the elongated shaft 71. The instrument handle 72 can latch to the instrument drive mechanism 75 to retain the medical instrument 70 for use during the procedure.

When attempting to dock the medical instrument 70 to the instrument drive mechanism 75, the drive inputs 73 of the instrument handle 72 and the drive outputs 74 of the instrument drive mechanism 75 may not be aligned. Misalignment of the drive inputs 73 and the drive outputs 74 can make docking the medical instrument 70 to the instrument drive mechanism 75 difficult or impossible. In order for the medical instrument 70 to dock to the instrument drive mechanism 75, the drive outputs 74 or the drive inputs 73 may need to be rotated until they are properly aligned.

There are several ways by which the drive outputs 74 and the drive inputs 73 can be aligned. For example, in some embodiments, the instrument drive mechanism 75 may be configured such that the motors are back drivable. In such embodiments, the force of docking the medical instrument 70 to the instrument drive mechanism 75 may be sufficient to cause the drive outputs 74 to rotate until they are adequately aligned with the drive inputs 73. In some embodiments, however, this may require significant force as any resistance in the motors must be overcome as they are back driven. Similarly, in some embodiments, the motors in the instrument drive mechanism 75 may be turned off during docking in order to allow the drive outputs 74 to rotate until they are aligned with the drive inputs 73. The performance provided by these embodiments may be adjustable. For example, the torque required to rotate the drive outputs 74 may be adjustable.

As another example, in some embodiments, the force applied during docking may cause the drive inputs 73 on medical instrument 70 to rotate until they are adequately aligned with the drive outputs 74 of the instrument drive mechanism 75. Some embodiments of medical instruments 70 may include pull wires that are actuated by the drive inputs 73 that are not pre-tensioned. For medical instruments 70 that do not include pre-tensioned pull wires, the drive inputs 73 may have some tolerance for free motion. That is, for medical instruments 70 that do not include pre-tensioned pull wires it may be possible to rotate the drive inputs 73 (at least for some degree of rotation) without actuating the pull wires. Therefore, in some embodiments, when the drive inputs 73 are misaligned with the drive outputs 74, the drive inputs 73 may rotate to adjust themselves within this tolerance during docking.

Other embodiments of medical instruments 70 may include pre-tensioned pull wires. For some embodiments of these instruments (which include pre-tensioned pull wires) any rotation of the drive inputs 73 can cause a corresponding actuation of the pull wires. For example, where the pre-tensioned pull wires are configured to cause articulation of the elongated shaft 71 of the instrument 70, any rotation of the drive inputs 73 will cause articulation of the elongated shaft 71. For these embodiments, it may be undesirable to permit the drive inputs 73 to rotate freely to facilitate alignment during docking. For example, it may be undesirable to permit the drive inputs 73 to rotate freely during docking because this rotation may cause the elongated shaft 71 to articulate, which may not be acceptable because it may desired that the elongated shaft 71 of the medical instrument 70 be maintained straight during docking. Therefore, a methodology to automatically adjust the drive outputs 74 to align with drive inputs 75 may be desirable. Examples of such a methodology are described in greater detail below.

In some embodiments, the instrument drive mechanism 75 can include sensors configured to sense torque or force applied on to the drive outputs 74. During docking of the medical instrument 70, if the drive outputs 74 and drive inputs 73 are misaligned, the drive inputs 73 can contact and push against the drive outputs 74 as the medical instrument 70 and instrument drive mechanism 75 are brought together. This contact between the drive outputs 74 and the drive inputs 73 that is experienced during misalignment can be determined based on the output of the sensors. For example, the misalignment can cause a torque to be imparted on the drive output 74 by the drive input 73 that can be measured by the sensors. The measured torque can provide an indication that the drive output 74 and the drive input 73 are misaligned. In some embodiments, the system may then activate the motor associated with the drive output 74, causing the drive output 74 to rotate. The drive output 74 can rotate until it is aligned with the drive input 73. In some embodiments, the system determines that the drive output 74 is aligned with the drive input 73 when the measured torque imparted on the drive output 74 decreases or drops to zero. When this occurs, the system can stop rotating the drive output 74.

Thus, in some embodiments, the system may be configured to automatically align drive outputs 74 with drive inputs 73 in response to torque or force measured by the sensors associated with the drive outputs 74, wherein the torque is caused by misalignment of the drive outputs 74 with drive inputs 73. This may advantageously facilitate docking of the medical instrument 70 to the instrument drive mechanism 75. In some embodiments, this advantageously enables alignment of drive outputs 74 with drive inputs 73 without requiring the motors associated with the drive outputs 74 be back driven. Further, in some embodiments, this advantageously enables alignment of drive outputs 74 with drive inputs 73 without requiring rotation of the drive inputs 73. Thus, in some embodiments, the automatic alignment system described herein may advantageously be used with medical instruments that include pre-tensioned pull wires.

These and other features and advantages of the disclosed systems and methods, will be described in greater detail below with reference to the examples and embodiments illustrated in FIGS. 21A-29. These examples and embodiments are provided by way of illustration and are not intended to limit this disclosure.

Figure 21A:
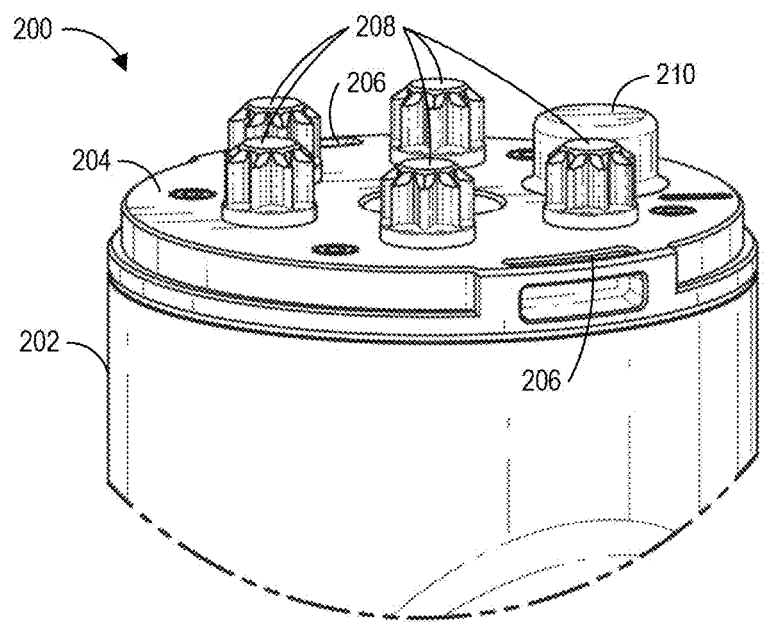
FIGS. 21A and 21B illustrate isometric and end views, respectively, of an embodiment of an instrument drive mechanism including a plurality of drive outputs configured to engage a corresponding plurality of drive inputs of a medical instrument.
Figure 21B:
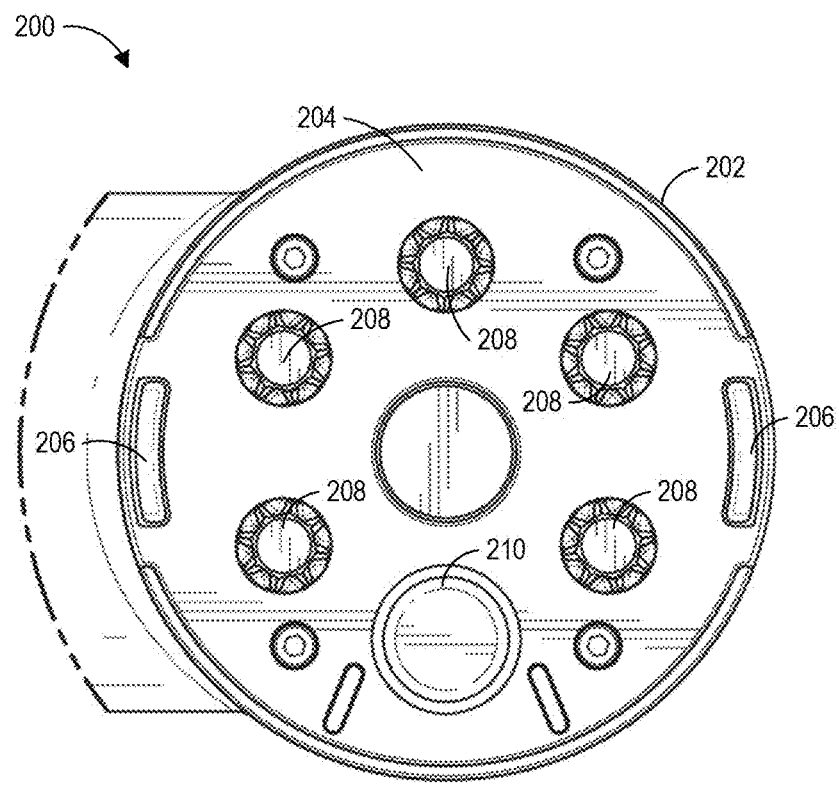

FIGS. 21A and 21B illustrate isometric and end views, respectively, of an embodiment of an instrument drive mechanism 200 including a plurality of drive outputs 208 configured to engage a corresponding plurality of drive inputs of a medical instrument. As illustrated, the instrument drive mechanism 200 can include a housing 202. The housing 202 can include an attachment face 204 that is configured to dock to the medical instrument. The instrument drive mechanism 200 can include latching mechanisms 206 that secure the medical instrument to the instrument drive mechanism 200 when docked.

As illustrated in FIGS. 21A-21B, the instrument drive mechanism 200 can include drive outputs 208. The drive outputs 208 can be, for example, rotatable elements configured to be driven by motors that are positioned, for example, within the housing. In the illustrated embodiment, the drive outputs 208 are configured as splines or gears that protrude from the attachment face 204, although other configurations for the drive outputs 208 are possible. For example, the drive outputs 208 can comprise receptacles or sockets that are formed as recesses into the attachment face 204. The drive outputs 208 are configured to couple with and engage corresponding drive inputs on the medical instrument. The drive outputs 208 transfer rotational motion (or other motion depending on the embodiment) from the motors in the instrument drive mechanism 208 to the drive inputs of the medical instrument such that the motors can be used to control the medical instrument during a procedure.

In some embodiments, the instrument drive mechanism 200 can include additional features, such as communication module 210. The communication module 210 can be configured to read information from a medical instrument that is docked to the instrument drive mechanism 200. In some embodiments, the communication module 210 (or some other portion of the instrument drive mechanism 200) comprises one or more proximity sensors. The proximity sensors may be configured to determine when a medical instrument is in the process of being or has been docked to the instrument drive mechanism. The proximity sensors may comprise one or more magnetic proximity sensors, for example.

Figure 22A:
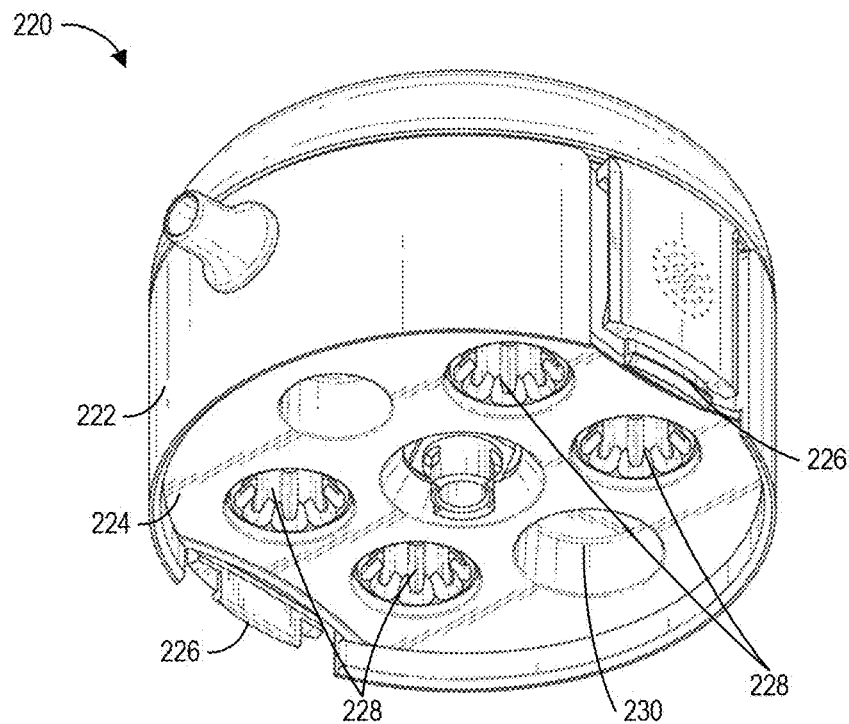
FIGS. 22A and 22B illustrate isometric and end views, respectively, of an embodiment of an instrument handle of a medical instrument including a plurality of drive inputs configured to engage a corresponding plurality of drive outputs of an instrument drive mechanism.
Figure 22B:
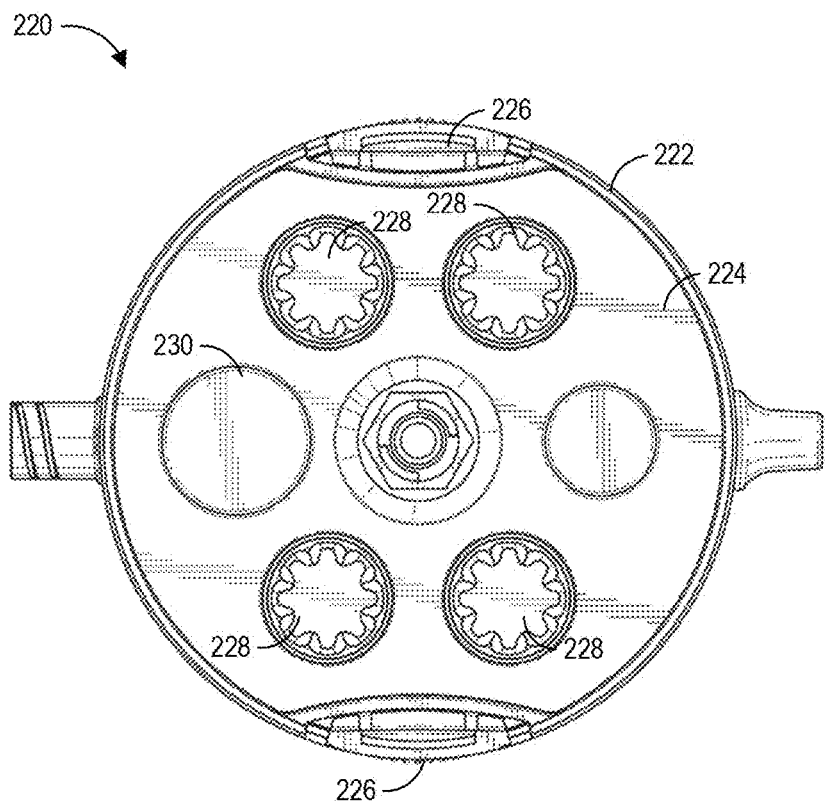

FIGS. 22A and 22B illustrate isometric and end views, respectively, of an embodiment of an instrument handle 220 of a medical instrument including a plurality of drive inputs 228 configured to engage the corresponding plurality of drive outputs 208 of the instrument drive mechanism 200. As illustrated, the instrument handle 220 can include a housing 222. The housing 222 can include an attachment face 224 that is configured to dock to the attachment face 204 of the instrument drive mechanism 200. The instrument handle 220 can include latching mechanisms 226 that secure the instrument handle 220 to the instrument drive mechanism 200 when docked.

As illustrated in FIGS. 22A-22B, the instrument handle 220 can include drive inputs 228. The drive inputs 228 can be rotatable elements configured to be driven by the drive outputs 208 of the instrument drive mechanism 200. In the illustrated embodiment, the drive inputs 228 are configured as receptacles or sockets that are recessed into the attachment face 224, although other configurations for the drive inputs 228 are possible. For example, the drive inputs 228 can comprise protruding splines or gears that extend from the attachment face 224.

In some embodiments, the instrument handle 220 can include additional features, such as communication module 230, which can be configured to transmit information to communication module 210 of the instrument drive mechanism 200. In some embodiments, the communication module 230 (or some other portion of the instrument handle 220) comprises one or more proximity sensors. The proximity sensors may be configured to determine when the medical instrument is in the process of being or has been docked to the instrument drive mechanism 200. The proximity sensors may comprise one or more magnetic proximity sensors.

Figure 23:
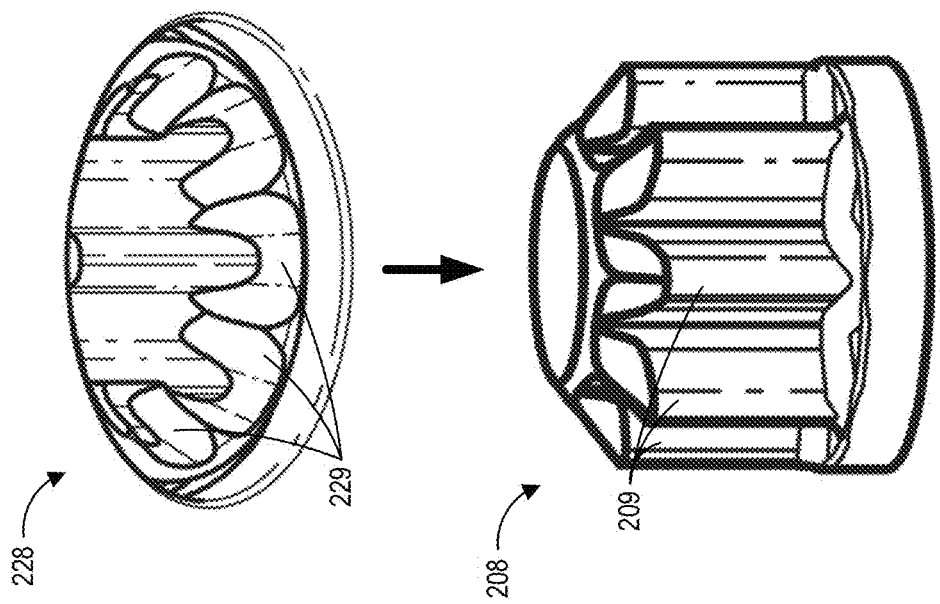
FIG. 23 illustrates a perspective view of an instrument drive output engaging an instrument drive output during docking of a medical instrument to an instrument drive mechanism.

FIG. 23 illustrates a perspective view of an embodiment of an instrument drive output 208 engaging the drive input 228 during docking of the instrument handle 220 to the instrument drive mechanism 200. As shown, the drive output 208 may comprise teeth 209 (e.g., ridges, protrusions, cutouts, indentations, etc.) that are configured to be received within corresponding grooves 229 of the drive input 229. In the illustrated example, the teeth 209 and grooves 229 interact to transfer rotational motion.

In many of the examples described below, the drive output 208 is illustrated as a gear comprising teeth 209, and the drive input 228 is configured as a socket comprising grooves 229. However, this need not be the case in all embodiments and many other structural arrangements for transferring rotational motion between the drive output 208 and the drive input 228 are possible. For example, in some embodiments, the drive output 208 may comprise a socket, and the drive input 228 can comprise a gear configured to be received in the socket. As another example, in some embodiments, both the drive output 208 and the drive input 228 can be configured as gears configured to mesh together. For ease of description, the following examples, continue to describe and illustrate the drive output 208 as a gear and the drive input 228 as a socket with the understanding that this is done by way of illustration and is not intended to limit the disclosure to the particular illustrated structural arrangement. In other embodiments, the drive outputs 208 and drive inputs 228 can be configured to transfer other types of motion, such as linear motion.

Figure 24:
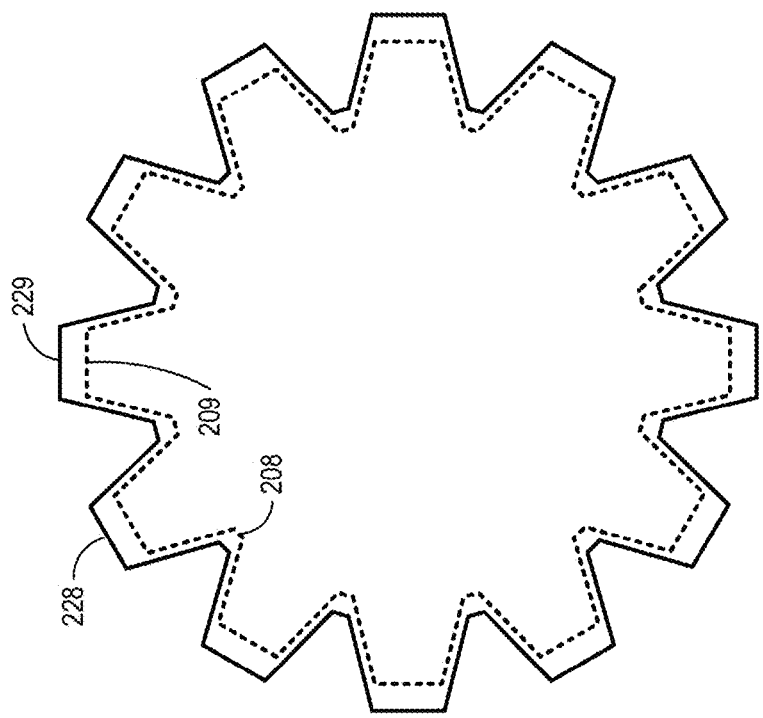
FIG. 24 illustrates an embodiment of a drive output aligned with an embodiment of a drive input.

FIG. 24 illustrates a view of an example where the drive output 208 is aligned with the drive input 228. As shown, when aligned, the teeth 209 of the drive output 208 may be received within the grooves 229 of the drive input 228. In some embodiments, because the teeth 209 are aligned within the grooves 229, the drive input 228 does not impart any torque or force on the drive output 208, or vice versa. This may be representative of a desired alignment between the drive input 228 and the drive output 208. The illustrated alignment may also facilitate docking of the medical instrument to the instrument drive mechanism because, when aligned, the drive output 208 can easily be received within the drive input 228.

Figure 25A:
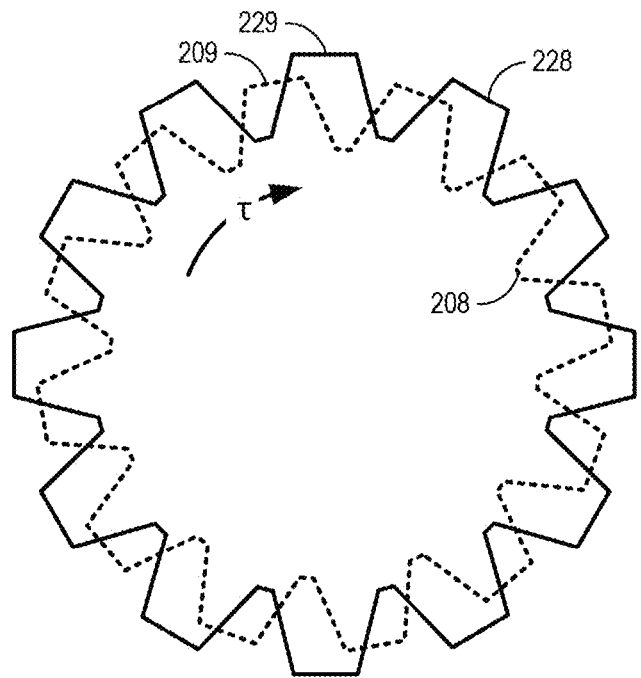
FIGS. 25A-25D illustrate alignment of a drive output with a drive input.
Figure 25B:
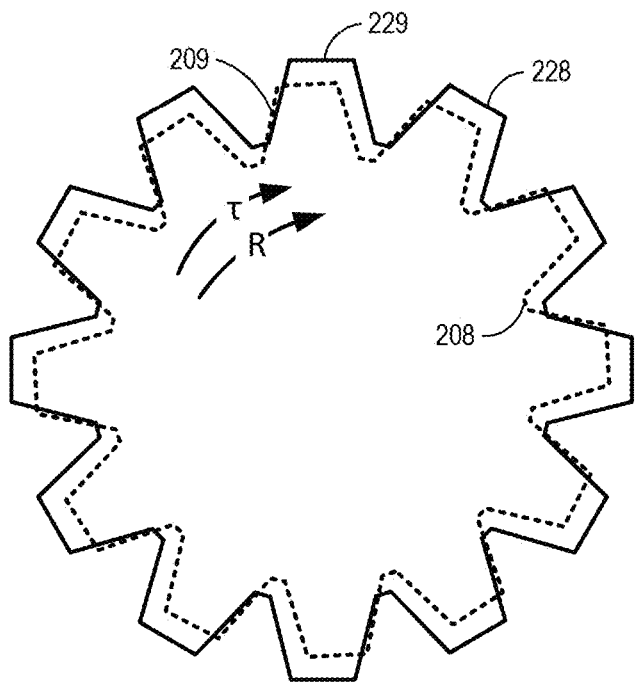
Figure 25C:
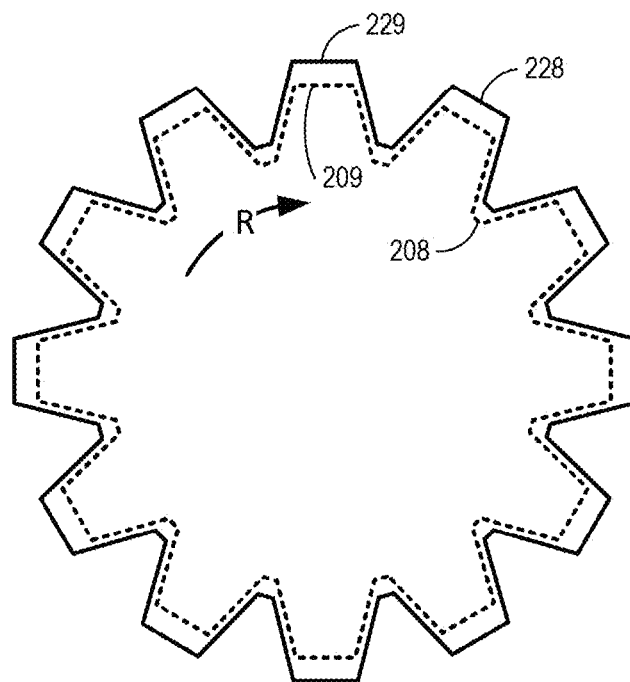
Figure 25D:
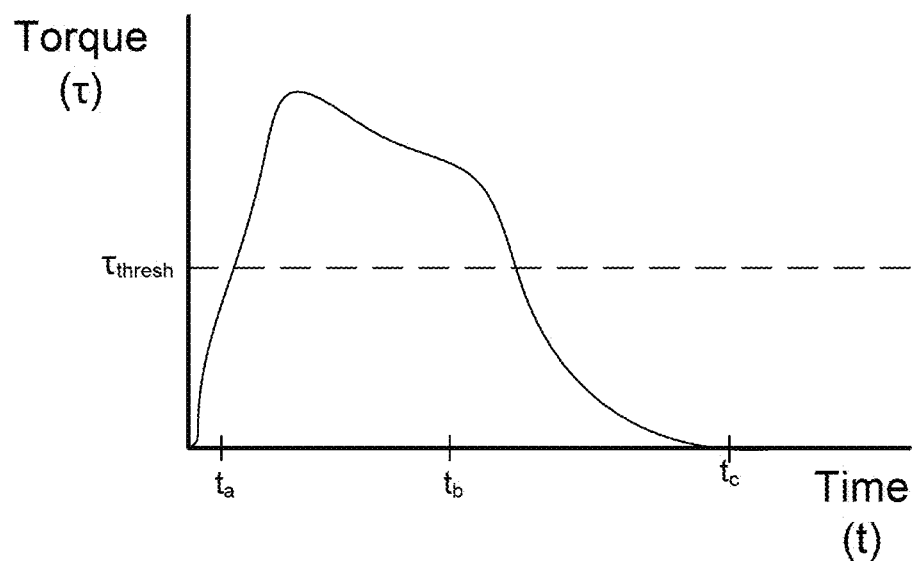

FIGS. 25A-25D illustrate an example alignment process that can be used to align the drive output 208 with the drive input 228 during docking of the medical instrument to the instrument drive mechanism. FIGS. 25A-25C illustrate example views of the drive output 208 and the drive input 228 at various stages during the process, and FIG. 25D illustrates an example graph showing the output of a torque sensor associated with the drive output 208 during the process.

As shown in FIG. 25A, frequently, when attempting to dock the medical instrument to the instrument drive mechanism, one or more drive output 208 of the instrument drive mechanism and one or more drive input 228 of the medical instrument will not be properly aligned. For example, the teeth 209 of the drive output 208 may be misaligned with the grooves 229 of the drive input 228 as illustrated in FIG. 25A. When this occurs, it may be difficult to fully dock the medical instrument to the instrument drive mechanism because the misalignment may prevent the medical instrument and the instrument drive mechanism from being fully brought together. Thus, it may be desirable to bring the drive output 208 and the drive input 228 into alignment.

When misaligned, the drive input 228 may impart a force on the drive output 208 that creates a torque τ as shown. The torque τ may be caused by the walls of the grooves 229 contact and pressing on the walls of the teeth 209 as the medical instrument is brought toward the instrument drive mechanism. This may be particularly true in embodiments where the medical instrument includes pre-tensioned pull wires, because in such medical instruments, the drive inputs 228 may not be permitted to freely rotate. Also, in some embodiments, the motor associated with the drive output 208 may not permit the drive output 208 to freely rotate, and thus the contact between the misaligned drive output 208 and the drive input 228 can generate the torque τ as shown. A signal indicative of the torque τ can be sensed or measured by a sensor (such as a torque or force sensor) associated with the drive output 208. In FIG. 25A, the torque τ is illustrated having a clockwise direction, although this need not be the case in all embodiments. For example, the torque τ can have a counterclockwise direction depending on how the drive output 208 and the drive input 228 are misaligned.

As shown in FIG. 25B, based on the torque τ, the drive output 208 can be rotated in a direction of rotation R that is the same as the direction of the torque τ so as to bring the drive output 208 into alignment with the drive input 228. At the stage illustrated in FIG. 25B, the drive output 208 has been rotated in the clockwise direction. As illustrated in FIG. 25B, the drive output 208 is still misaligned with the drive input 228; however, the misalignment is lessened (when compared to FIG. 25A) because of the rotation R. The rotation R can be driven by the motor associated with the drive output 208 in response to the measured torque τ as discussed throughout this application.

As illustrated in FIG. 25C, the rotation R of drive output 208 can continue until the drive output 208 is aligned with the drive input 228. At this stage, as illustrated in FIG. 25C, the torque τ is no longer imparted on the drive output 208 because the drive output 208 and the drive input 228 are aligned. As shown, when aligned, the teeth 209 of the drive output 208 can be aligned with the grooves 229 of the drive input 228. Because the teeth 209 of the drive output 208 are aligned with the grooves 229 of the drive input 228, the drive input 228 may not impart torque τ. This may trigger the motor to stop rotating the drive output 208. With the drive output 208 and the drive input 228 aligned, docking of the medical instrument to the instrument drive mechanism may be facilitated.

FIG. 25D illustrates an example graph of the output of the torque or force sensor associated with the drive output 208 during the docking and alignment process illustrated in FIGS. 25A-25C. In the illustrated embodiment, the graph illustrates measured torque, although this need not be the case in all embodiments. For example, the graph could be representative of measured force or torque, or an output of the sensor that is indicative of torque or force.

As shown in FIG. 25D, initially, the measured torque τ is substantially zero. This may be representative of a state in which the medical instrument is not contacting the instrument drive mechanism. In this state, nothing is contacting the drive output 208, so the torque sensor associated with the drive output 208 does not measure any torque. As illustrated, the measured torque may begin to rise as the medical instrument is brought into contact with the instrument drive mechanism during docking because the misaligned drive output 208 may begin to contact to the drive input 228.

At time $t_a$ illustrated in FIG. 25D, which may be representative of the state shown in FIG. 25A, the torque τ has risen but is still below a threshold $\tau_{thresh}$. In some embodiments, while the measured torque τ remains below the threshold $\tau_{thresh}$, rotation of the drive output 208 is not triggered. The threshold $\tau_{thresh}$ may be selected to account for noise and to adjust the sensitivity of the system.

From time $t_a$ the measured torque τ may continue to increase beyond the threshold $\tau_{thresh}$. Once the measured torque τ exceeds the threshold $\tau_{thresh}$, rotation R of the drive output 208 can be triggered. For example, time $t_b$ may be indicative of the stage illustrated in FIG. 25B, at which, as discussed above, the drive output 208 is still misaligned with the drive input 228, the measured torque τ is still present, and the drive output 208 is undergoing rotation R so as to align the drive output 208 with the drive input 228.

As illustrated in FIG. 25D, from time $t_b$ the measured torque τ continues to decrease until the measured torque τ falls below the threshold $\tau_{thresh}$. When the measured torque $\tau$ falls below the threshold $\tau_{thresh}$ the rotation R may stop because the drive output 208 and the drive input 228 are now aligned as shown in FIG. 25C, which may be indicative of the time $t_c$. The time $t_c$ can correspond to proper alignment as shown, for example, in FIG. 25C.

Figure 26:
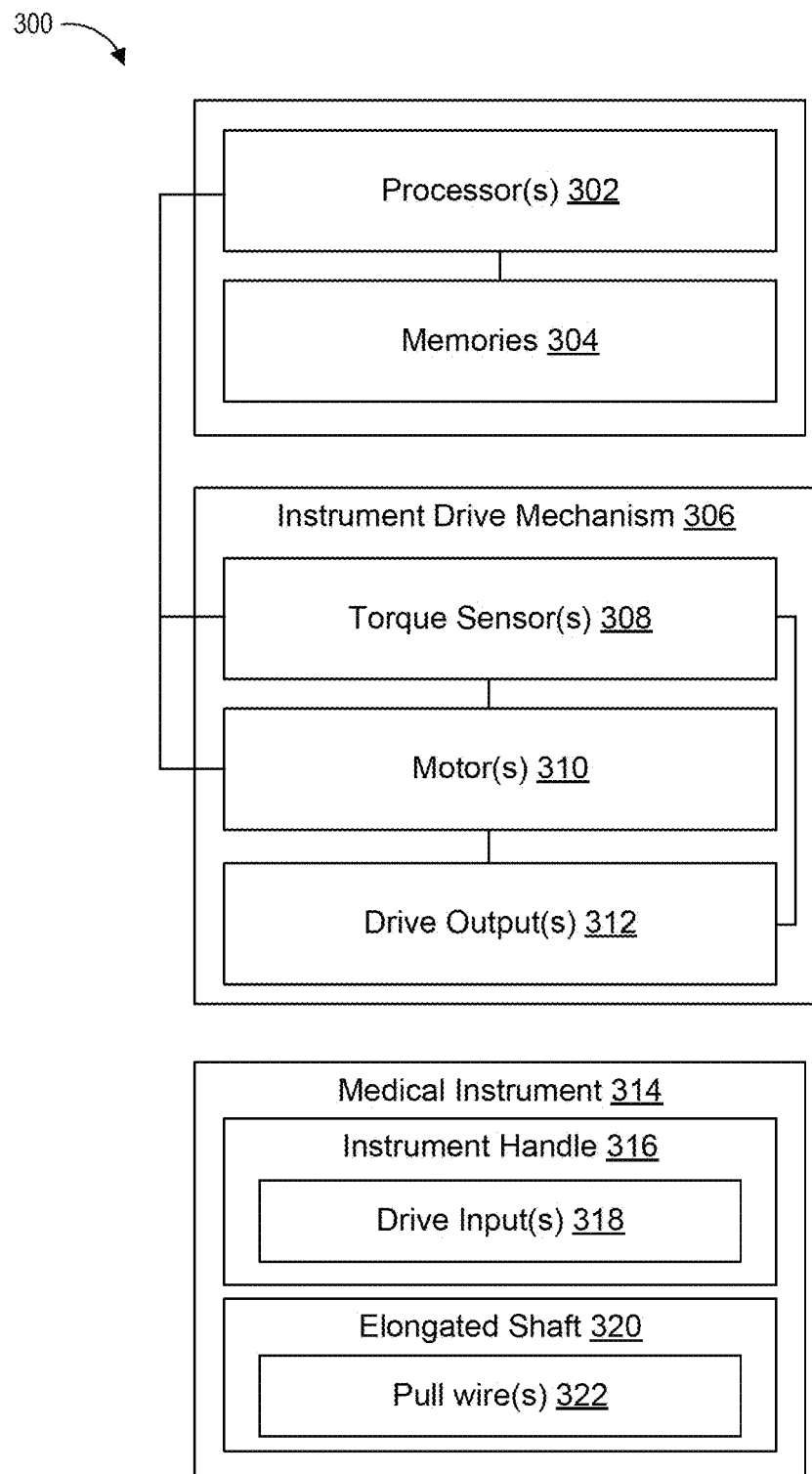
FIG. 26 is a block diagram illustrating an embodiment of a medical system configured to align drive outputs of an instrument drive mechanism with drive inputs of a medical instrument.

FIG. 26 is a block diagram illustrating an embodiment of a medical system 300 configured to align drive outputs 312 of an instrument drive mechanism 306 with drive inputs 318 of a medical instrument 314. In some embodiments, alignment may occur automatically based on the output of torque or force sensors 308 associated with the drive outputs 312 in a manner similar to that which has been described with reference to FIGS. 25A-25D, as well as will be described in greater detail below with reference to FIG. 27.

As illustrated in FIG. 26, the system 300 may include one or more processors 302 and one or more computer readable medium or memories 304 in communication with the processors 302. The memories 304 may be configured with instructions that configure the processors 302 to perform various features. For example, the memories 304 can be configured with instructions that cause the processors 302 to perform the automatic alignment and docking features described throughout the application.

The system 300 also includes an instrument drive mechanism 306. Example instrument drive mechanisms have been described above, for example, with reference to FIGS. 15, 16, 21A and 21B. In some embodiments, the instrument drive mechanism 306 is positioned on a distal end of a robotic arm or other instrument positioning device. The instrument drive mechanism 306 can be configured to dock with a medical instrument 314. In the illustrated embodiment, the instrument drive mechanism 306 includes torque sensors 308, motors 310, and drive outputs 312. The instrument drive mechanism 306 may also include additional features that are not illustrated in FIG. 26 (e.g., proximity sensors, communication modules, etc.).

As discussed previously, the drive outputs 312 can be configured to engage with corresponding drive inputs 318 on the medical instrument 314. The drive outputs 312 can be driven by motors 310. The motors 310 can be configured to cause the drive outputs 312 to rotate, for example, in clockwise and counterclockwise directions. The drive outputs 312 can be configured to transfer the rotational motion of the motors 310 to the drive inputs 318 of the medical instrument 314. As such, the drive outputs 312 can comprise any structure suitable for transferring rotational motion, including, for example, gears and sockets, among others.

As shown in FIG. 26, the instrument drive mechanism 306 can also include sensors 308, such as the illustrated torque sensors 308. As mentioned previously, other types of sensors, such as force sensors may also be used. The torque sensors 308 can be associated with the drive outputs 312. For example, the torque sensors 308 may provide an output signal that is indicative of torque or force imparted on the drive outputs 312. In some embodiments, the torque sensors 308 can comprise one or more strain gauges. The torque sensors can be positioned between the housing of the instrument drive mechanism 306 and the motors 310. In some embodiments, the torque sensors 308 are bi-directional. That is, in some embodiments, the torque sensors 308 may be configured to measure torque in both clockwise and counter clockwise directions. The output signals of the torque sensors 308 may be indicative of the direction of the torque imparted on the drive outputs 312.

As shown, the torque sensors 308 and motors 310 can be communicatively coupled to the processors 302. This may allow, for example, the output signals of the torque sensors 308 to be used by the processors 302, and may further allow the processors 302 to control the motors 310. In some embodiments, the processors 302 control the motors 310 based on the output signals of the torque sensors 308 to implement the automatic alignment and docking features described herein.

FIG. 26 illustrates that the system 300 can also include the medical instrument 314. Example medical instruments 314 are described above, for example, with reference to FIGS. 1, 3-5, 8, 9, 16-18, 22A, and 22B. The medical instrument 314 can include an instrument base or handle 316 and an elongated shaft 320. The instrument handle 316 can be configured to dock to the instrument drive mechanism 306. The elongated shaft 320 can extend from the instrument handle 316. In some embodiments, the elongated shaft 320 can be configured for insertion into a patient's body (e.g., laparoscopically or endoscopically) during a medical procedure.

The instrument handle 316 can include drive inputs 318 configured to engage with the drive outputs 312 of the instrument drive mechanism 306. In some embodiments, the drive inputs 318 are associated with one or more pull wires 322 that are actuable to perform various functions with the medical instrument 314. For example, in some embodiments, actuating the pull wires 322 articulates the elongated shaft 320 or operates a tool positioned at the distal end of the elongated shaft 320. In some embodiments, the pull wires 322 are actuated by rotating the drive inputs 318. As noted above, the drive inputs 318 may be configured to engage the drive outputs 312 such that rotational motion from the motors 310 can be transmitted from through the drive outputs 312 to the drive inputs 318 to actuate the pull wires 322. In some embodiments, the pull wires 322 may be pre-tensioned.

In some embodiments, the medical instrument 314 comprises pre-tensioned pull wires. That is, in some embodiments, any rotation of the drive inputs 318 causes actuation of the pull wires. In such embodiment, inadvertent or unintentional rotation of the drive inputs 318 can be undesirable as such rotation can cause inadvertent or unintentional articulation of the medical instrument.

In some embodiments, the system 300 is configured to implement an alignment process for automatically aligning drive outputs 312 and drive inputs 318 to facilitate docking.

Figure 27:
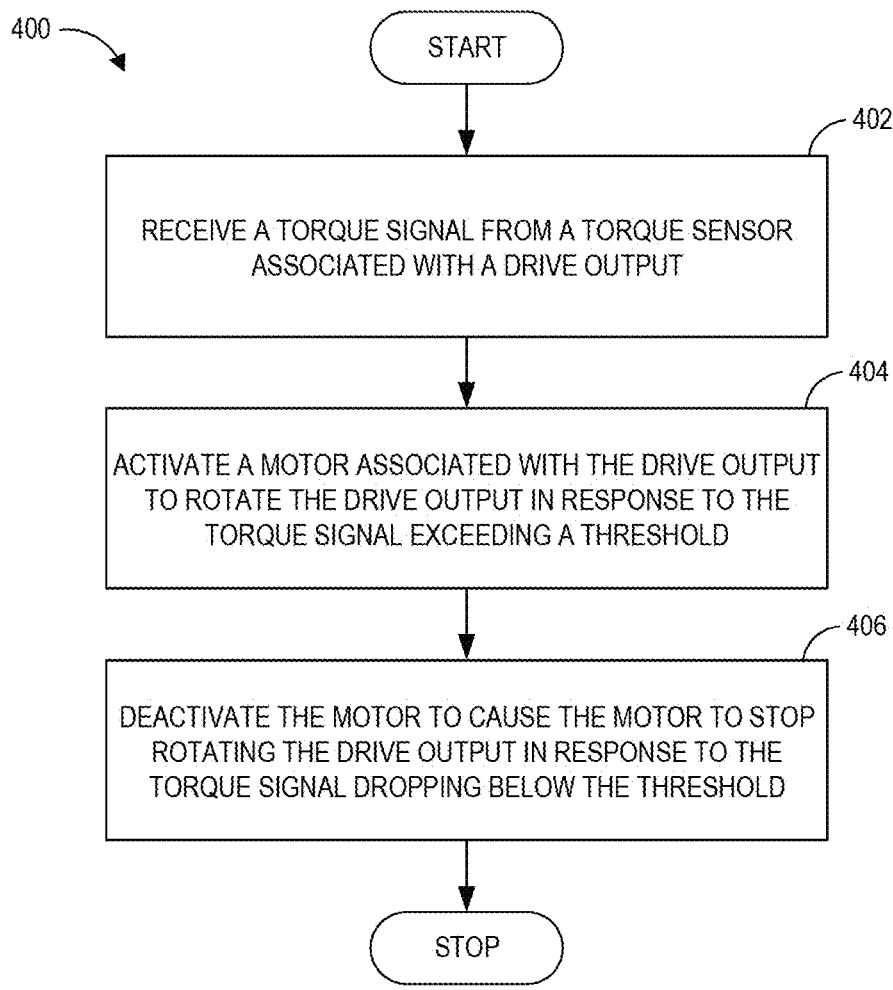
FIG. 27 is a flowchart illustrating an example method for aligning drive outputs of an instrument drive mechanism with drive inputs of a medical instrument.

FIG. 27 is a flowchart illustrating an example method 400 of alignment of drive outputs of an instrument drive mechanism with drive inputs of a medical instrument. In some embodiments, the method 400 can be implemented on the system 300 of FIG. 26, as well as on other medical systems described herein.

The method 400 begins at block 402, at which a torque signal is received from a torque sensor associated with a drive output of the instrument drive mechanism. In some embodiments, the torque signal may be indicative of a direction of the torque imparted on the drive output. The torque may, in some embodiments, be caused by misalignment between the drive output and the drive input as described above. In some embodiments, the method 400 may use a signal indicative of force, rather than torque.

Next, the method 400 moves to block 404, at which a motor associated with the drive output is activated to rotate the drive output in response to the torque signal (received at block 402) exceeding a threshold. The threshold may be configured so as to adjust the sensitivity of the system and/or account for noise in the signal. In some embodiments, the threshold may be configured based on the medical instrument. For example, stiffer medical instruments may include a higher threshold than more flexible medical instruments. In some embodiments, threshold information is stored for each instrument (in some embodiments, on the instrument itself) and read for use in the method 400.

In some embodiments, the rotation is configured to align the drive output with the drive input. In some embodiments, the drive output is rotated in the same direction as the torque imparted on the drive output. For example, if the torque is in the clockwise direction, the drive input may be rotated in the clockwise direction. In some embodiments, the drive output is configured to be rotated in a direction that is opposite the direction of the torque.

In some embodiments, the speed of the rotation can be proportional to the magnitude of the torque measured at block 402. For example, the greater the torque, the greater the speed of rotation. Because the torque may be related to the degree of misalignment, the rotation may be faster when the drive outputs and drive inputs are significantly misaligned, and the rotation may slow as the drive outputs and drive inputs are rotated into alignment. In other embodiments, the speed of rotation may be constant.

The method 400 then moves to block 406, at which the motor is deactivated to cause the motor to stop rotating the drive output in response to the torque signal dropping below the threshold. The torque signal dropping below the threshold may be indicative of proper alignment between the drive output and the drive input.

In some embodiments, the method 400 is performed during an instrument docking or instrument load state. For example, the method 400 may, in some embodiments, be performed while docking the medical instrument to the instrument drive mechanism. In some embodiments, determining whether the system is in an instrument load state can be automatic, for example, based on proximity sensors in the instrument drive mechanism and the medical instrument, or manual, based on user input. In some embodiments, once docking is completed, the system exits the instrument load state and no longer performs the method 400.

In some embodiments, the method 400 may be performed for each drive output of the instrument drive mechanism, and thus may be used to align a plurality of drive outputs with a plurality of drive inputs.

FIGS. 28A-28D illustrate an example homing process using the drive output 208 and the drive input 228 described above. In some embodiments, the homing process is completed after the medical instrument has been docked to the instrument drive mechanism. The homing process may be used to estimate or determine the size of a gap g between the teeth 209 of the drive output 208 and the grooves 229 of the drive input 228. The gap g may represent a clearance or tolerance between the drive output 208 and the drive input 228. As described below, it may be desirable to compute the size of the gap g so that it can be accounted for while controlling a robotic medical instrument.

Figure 28A:
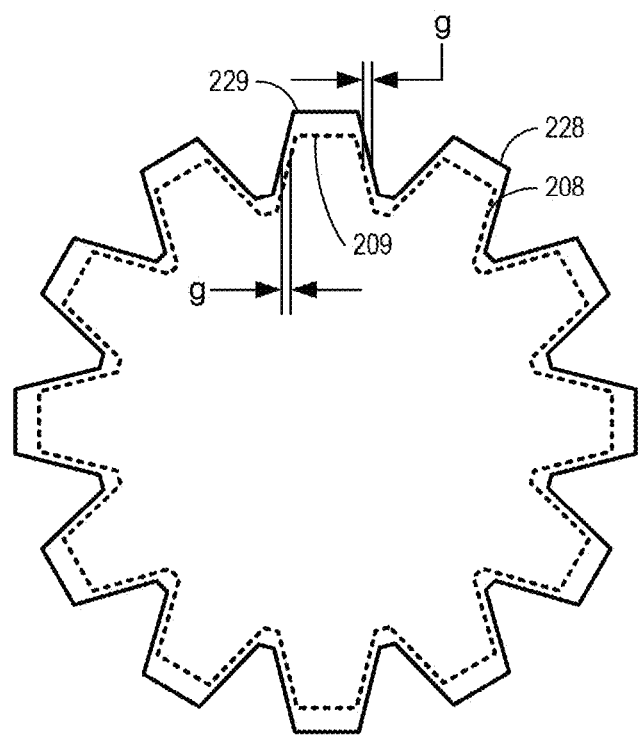
FIGS. 28A-28D illustrate an example homing process using a drive output and drive input.

FIG. 28A illustrates the drive output 208 engaged with the drive input 228. As shown, the teeth 209 of the drive output 208 are received within the grooves 229 of the drive input 228. For tolerance and clearance reasons, a gap g may exist between the teeth 209 and the grooves 229. The gap g may facilitate docking and fit between drive output 208 and the drive input 228. As shown, the gap g can exist on one or both sides of the teeth 209. For example, the entire gap g may exist on a first side, the entire gap g may exist on a second side, or a portion of the gap g can exist on the first side and another portion of the gap g can exist on the second side of the teeth 209. Because of the gap g, it may be possible to rotate the drive output 208 without causing a corresponding rotation of the drive output 208. For example, the drive output 208 must be rotating until a wall of the teeth 209 contacts a wall of the groove 229 before the drive output 208 will begin rotating. As such, it may be desirable to determine or estimate the size of the gap g so that this distance can be accounted for. The gap g may be referred to as backlash. It may be desirable to account for the backlash when switching rotational directions. For example, after being rotated in the clockwise direction, it is necessary to rotate in the counterclockwise through the distance of the gap g before counterclockwise rotation will cause actuation of the medical instrument.

Figure 28B:
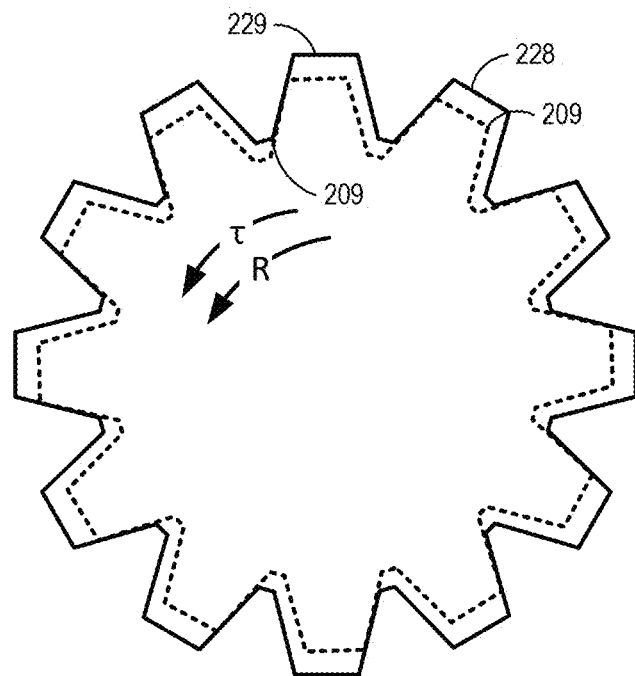

FIG. 28B illustrates that, as part of the homing process that determines the size of the gap g, the drive output 208 can be rotated in a first direction to a first rotational position. In the illustrated example, the drive output 208 is rotated with rotation R in a counterclockwise direction until a torque τ is measured in the same direction as the rotation R. The torque τ can be caused by the tooth 209 contacting the groove 229. In this manner, the process can determine the rotational position at which the tooth 209 will contact the groove 229 when rotated in the first direction.

Figure 28C:
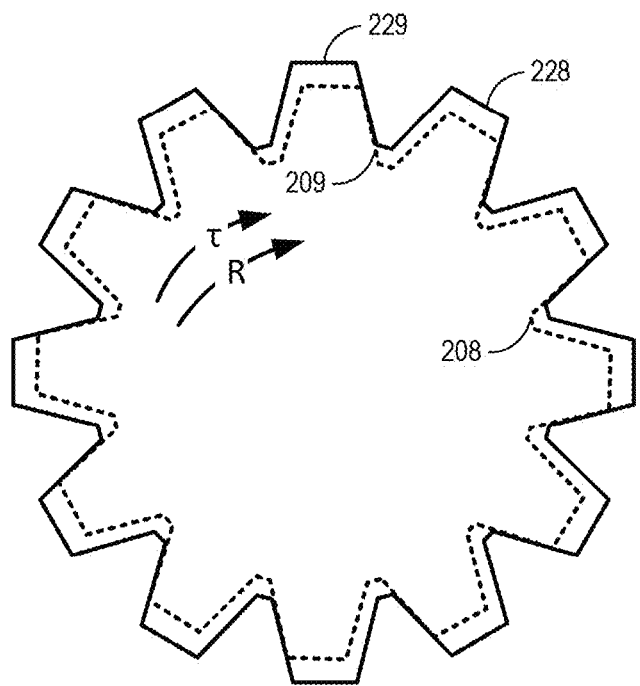

As shown in FIG. 28C, the drive output 208 can then be rotated in a second direction to a second rotational position. In the illustrated example, the drive output 208 is then rotated with rotation R in the clockwise direction until a torque τ is measured in the same direction as the rotation R. Again, the torque τ can be caused by the tooth 209 contacting the groove 229. In this manner, the process can determine the rotational position at which the tooth 209 will contact the groove 229 when rotated in the second direction.

The rotational distance between the first rotational position (shown in FIG. 28B) and the second rotational position (shown in FIG. 28C) can then be determined and used as the gap g. This is because the drive output 208 has been homed by locating each sidewall of the grooves 229 of the drive input 228. The rotational distance can then be used to account for backlash in the system when changing rotational directions.

Figure 28D:
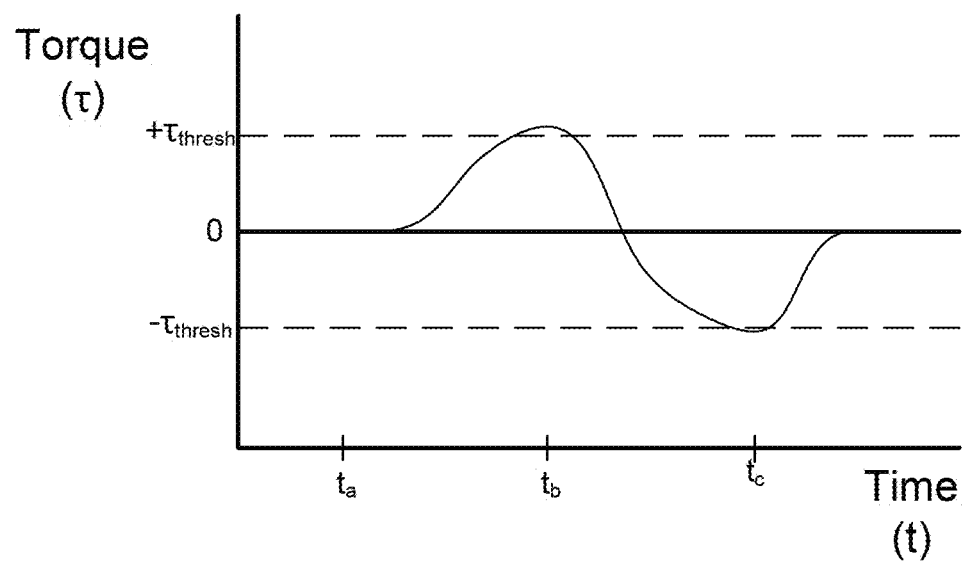

FIG. 28D illustrates an example graph of the output of a torque sensor associated with the drive output during the homing process illustrated in FIGS. 28A-28C. As before, the graph could alternatively represent force or an output signal indicative of force or torque. As shown, at time $t_a$ (representative of the state of FIG. 28A) the torque τ is substantially zero because the drive output 208 and the drive input 228 are aligned. At time $t_b$ (representative of the state of FIG. 28B) the torque τ has increased above a torque threshold +$τ_{thresh}$ indicating contact with the drive output 208. At time $t_c$ (representative of the state of FIG. 28C), the torque τ has decreased to the threshold −$τ_{thresh}$ indicating contact with the drive input 228 in the opposite direction. In the graph, the positive and negative torque thresholds $τ_{thresh}$ are indicative of limits in opposite rotational directions.

Figure 29:
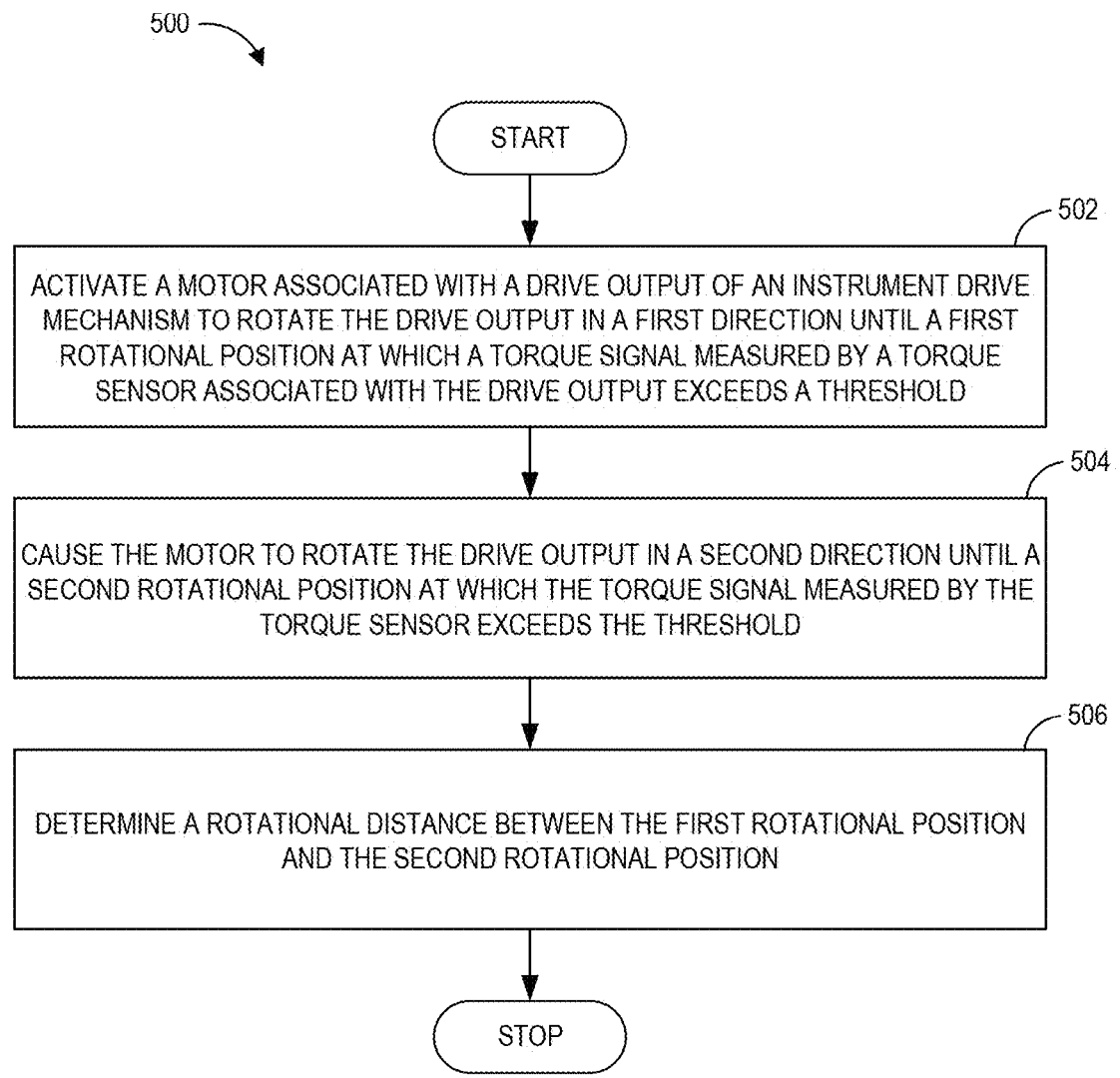
FIG. 29 is a flowchart illustrating an example homing method for a medical system.

FIG. 29 is a flowchart illustrating an example homing method 500 for a medical system. The medical system can be, for example, the medical system 300 of FIG. 26, as well as other medical systems described herein. The homing method 500 can be used to determine or estimate a gap between a drive input and a drive output as described with reference to FIG. 28A, such that the gap can be accounted for during further use of the medical system.

The method 500 begins at block 502, at which a motor associated with a drive output of the instrument drive mechanism is activated to rotate the drive output in a first direction until a first rotational position at which a torque signal measured by a torque sensor associated with the drive output exceeds a threshold. In some embodiments, the torque signal exceeding the threshold can be indicative of the drive output contacting the drive input, for example, as shown in FIG. 28B.

Next, the method 500 moves to block 504, at which the motor rotates the drive output in a second direction until a second rotational position at which the torque signal measured by the torque sensor exceeds the threshold. In some embodiments, the torque signal exceeding the threshold can be indicative of the drive output contacting the drive input in the opposite direction, for example, as shown in FIG. 28C.

Finally, at block 506, the method 500 determines the rotational distance between the first rotational position (FIG. 28B) and the second rotational position (FIG. 28C). The rotational distance can be representative of the gap or clearance between the drive output and the drive input.

In some embodiments, once the method 500 determines the gap, the gap is accounted for in future commanded motions. For example, rotation of the drive outputs is used to control the medical instrument. However, when rotation of the drive outputs changes directions, the drive output must be rotated back through the gap distance before it contacts the drive input in the opposite direction.

Figure 30:
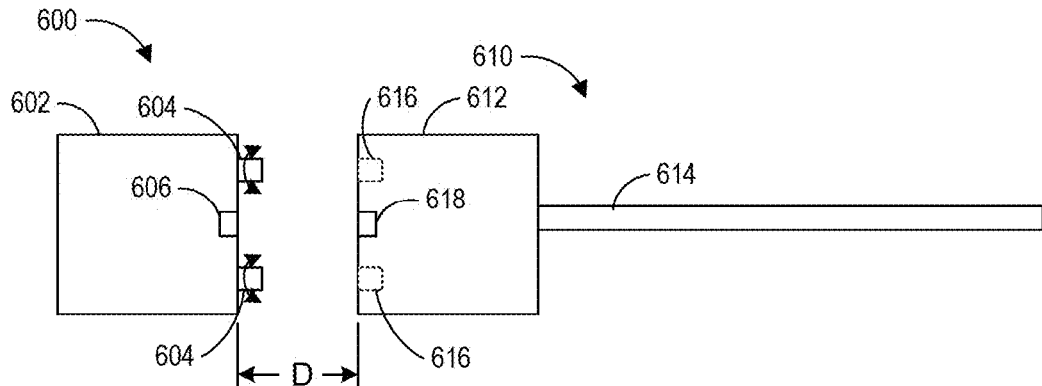
FIG. 30 illustrates an example of a robotic medical system during docking of the medical instrument to an instrument drive mechanism.

FIG. 30 illustrates an example of a robotic medical system 600 during docking of a medical instrument to an instrument drive mechanism. In the illustrated embodiment, the system 600 includes an instrument drive mechanism 602 and a robotic medical instrument 610. The robotic medical instrument 610 includes an instrument base or handle 612 and an elongated shaft 614. The elongated shaft 614 can be configured to articulate. In some embodiments, the elongated shaft includes one or more pull wires that are actuable to cause articulation of the elongated shaft 614. In some embodiments, the pull wires are pre-tensioned pull wires.

The robotic medical instrument 610 can be configured to dock to the instrument drive mechanism 602 such that the instrument drive mechanism 602 can drive the robotic medical instrument 610. As illustrated, the instrument drive mechanism 602 includes instrument drive outputs 604. The instrument drive outputs 604 can be configured to engage with corresponding instrument drive inputs 616 on the base or handle 612 of the robotic medical instrument 610. As described above, alignment between the drive outputs 604 and drive inputs 610 can facilitate docking.

In the illustrated example of FIG. 30, the instrument drive mechanism 600 includes a sensor 606. The sensor 606 can be configured to determine when the robotic medical instrument 610 is within a threshold loading distance D of the instrument drive mechanism 602. In some embodiments, the sensor 606 is a proximity sensor, a magnetic sensor, an RFID reader, or any other type of suitable sensor for determining when the robotic medical instrument is within the distance D of the instrument drive mechanism 602. In some embodiments, the instrument drive mechanism includes a corresponding sensor 618 that can be read by the sensor 606 of the instrument drive mechanism 602. For example, the sensor 618 can be a magnet or RFID tag that can be read by the sensor 606 when within the distance D. In some embodiments, the distance D is is at least 20 cm, at least 15 cm, at least 10 cm, at least 5 cm, or at least 1 cm. In some embodiments, the distance D is no more than 20 cm, no more than 15 cm, no more than 10 cm, no more than 5 cm, or no more than 1 cm.

In the illustrated embodiment, when the robotic medical instrument 610 is brought within the distance D of the instrument drive mechanism 602, motors of the instrument drive mechanism 602 can begin to drive oscillation of the drive outputs 604. For example, the oscillation of the drive output can include rotation of the drive output back and forth in clockwise and counter clockwise directions (as illustrated in FIG. 30 with arrows) through a rotational range of at least 30 degrees, at least 20 degrees, at least 15 degrees, at least 10 degrees, at least 5 degrees, at least 3 degrees, or at least 1 degree. In some embodiments, the oscillation is in a rotational range of no more than 30 degrees, no more than 20 degrees, no more than 15 degrees, no more than 10 degrees, no more than 5 degrees, no more than 3 degrees, or no more than 1 degree.

In some embodiments, when the instrument drive mechanism 602 is within the threshold docking distance D of the robotic medical instrument, the motors that drive the drive outputs can be placed in an admittance mode. For example, the motors can be in admittance mode while the drive outputs 604 oscillate.

Oscillation of the drive outputs 604 can facilitate alignment between the drive outputs and the drive inputs 616, which can allow the medical instrument 610 to dock to the instrument drive mechanism 602. In some embodiments, the system can determine that the robotic medical instrument has docked to the instrument drive mechanism based on an output of the sensor, and stop causing oscillation of the drive output when the robotic medical instrument has docked.

Figure 31:
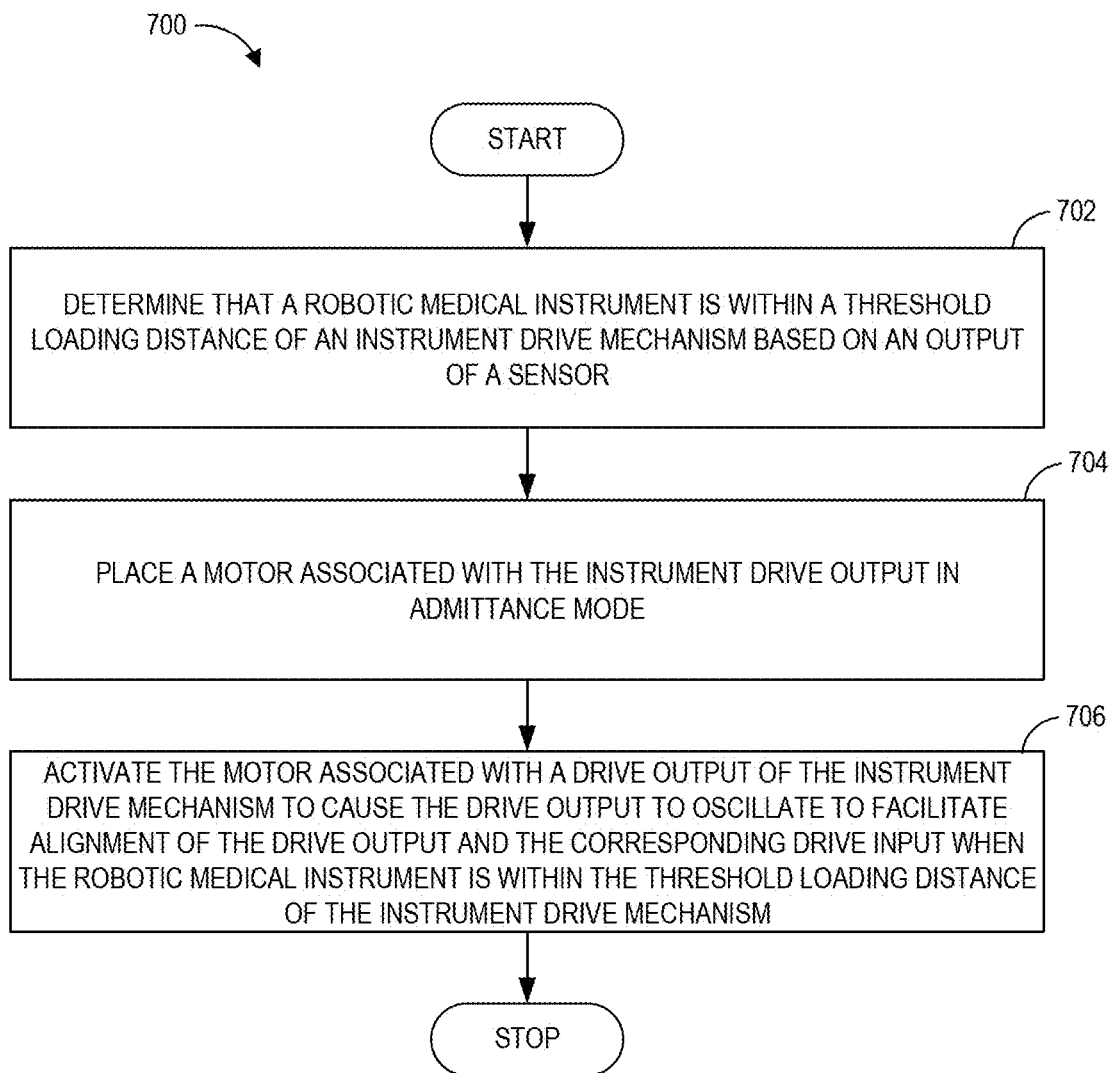
FIG. 31 is a flowchart illustrating an example alignment method for a robotic medical system.

FIG. 31 is a flowchart illustrating an example alignment method 700 for a robotic medical system. The method 700 can begin at block 702. At block 702, the method 700 includes determining that a robotic medical instrument is within a threshold loading distance of an instrument drive mechanism based on an output of a sensor on the instrument drive mechanism. This can be done with a sensor as described above. At block 704, the method 700 includes placing the motor associated with the drive input in an admittance mode. At block 706, the method 700 includes activating a motor associated with a drive output of the instrument drive mechanism to cause the drive output to oscillate to facilitate alignment of the drive output and the corresponding drive input when the robotic medical instrument is within the threshold loading distance of the instrument drive mechanism.

In some embodiments, the systems and techniques for medical instrument docking described above can be considered as admittance control of the joints of the instrument drive mechanism with input force/torque coming from the misalignment between driving gears and sockets.

3. Implementing Systems and Terminology.

Implementations disclosed herein provide systems, methods and apparatus for docking medical instruments, and in some embodiments, for docking robotic medical instruments that may include one or more pre-tensioned pull wires to instrument drive mechanisms. The systems, methods, and apparatus may facilitate alignment of drive outputs on the instrument drive mechanism with drive inputs on the medical instrument.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes/functions described herein may be stored as one or more instructions on a processor-readable or computer-readable medium. The term "computer-readable medium"

refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic medical system, comprising:
    an instrument drive mechanism comprising
        a drive output configured to rotate and engage a corresponding drive input on a handle of a robotic medical instrument, wherein the robotic medical instrument comprises a pre-tensioned pull wire actuated by the drive input,
        a motor associated with the drive output and configured to rotate the drive output, and
        a torque sensor associated with the drive output and configured to measure torque imparted on the drive output; and
    at least one computer-readable memory in communication with at least one processor, the memory having stored thereon computer-executable instructions that cause the at least one processor to, during docking of the handle of the robotic medical instrument to the instrument drive mechanism, activate the motor associated with the drive output to rotate the drive output in response to a torque signal from the torque sensor associated with the drive output.

2. The system of claim 1, wherein the instructions cause the processor to rotate the drive output to align the drive output with the corresponding drive output.

3. The system of claim 1, wherein the instructions cause the processor to activate the motor in response to the torque signal exceeding a threshold.

4. The system of claim 3, wherein the instructions cause the processor to deactivate the motor in response to the torque signal dropping below the threshold.

5. The system of claim 1, wherein the torque signal is indicative of a direction of a torque imparted on the drive output, and wherein the instructions cause the processor to activate the motor to cause rotation of the motor in a direction that is the same as the direction of the imparted torque.

6. The system of claim 1, wherein a speed of rotation of the motor is proportional to a measured torque determined based on the torque signal.

7. The system of claim 1, wherein a speed of rotation of the motor is constant.

8. The system of claim 1, wherein the drive output is a gear and the drive input is a socket.

9. The system of claim 1, wherein the drive output is a socket and the drive input is a gear.

10. The system of claim 1, wherein the instructions cause the processor to activate the motor associated with the drive output to rotate the drive output in response to the torque signal when the system is in a load instrument state.

11. The system of claim 1, wherein the torque sensor comprises a strain gauge.

12. The system of claim 11, wherein the strain gauge is positioned between a housing of the instrument drive mechanism and the motor.

13. The system of claim 1, wherein the torque sensor is bi-directional.

14. A computer readable medium comprising instructions configured to cause at least one processor to:
    during docking of a handle of a robotic medical instrument to an instrument drive mechanism, receive a torque signal from a torque sensor associated with a drive output of the instrument drive mechanism;
    activate a motor associated with the drive output to rotate the drive output in response to the torque signal from the torque sensor exceeding a threshold; and
    deactivate the motor to cause the motor to stop rotating the drive output in response to the torque signal from the torque sensor dropping below the threshold.

15. The computer readable medium of claim 14, wherein the instructions are configured to cause at least one processor to rotate the drive output to align the drive output with a drive input or a robotic medical instrument, wherein the robotic medical instrument comprises at least one pre-tensioned pull wire associated with the drive input.

16. The computer readable medium of claim 14, wherein the torque signal is indicative of a direction of a torque imparted on the drive output, and wherein the instructions cause the at least one processor to activate the motor to cause rotation of the motor in a direction that is the same as the direction of the imparted torque.

17. The computer readable medium of claim 14, wherein the instructions are configured to cause the motor to rotate the drive output at a speed of rotation that is proportional to a measured torque determined based on the torque signal.

18. The computer readable medium of claim 14, wherein the instructions are configured to cause the motor to rotate the drive output at a speed of rotation that is constant.

19. The computer readable medium of claim 14, wherein the instructions cause the at least one processor to activate the motor associated with the drive output to rotate the drive output in response to the torque signal when the system is in a load instrument state.

20. A method for aligning a drive output of an instrument drive mechanism with a drive input of a robotic medical instrument, the method comprising:
    during docking of a handle of the robotic medical instrument to the instrument drive mechanism, receiving a torque signal from a torque sensor associated with the drive output of the instrument drive mechanism, the torque signal indicative of a torque imparted on the drive output;
    comparing the torque signal to a threshold;
    activating a motor of the instrument drive mechanism associated with the drive output to cause rotation of the drive output in response to the torque signal exceeding the threshold; and
    deactivating the motor to cause the motor to stop rotating the drive output in response to the torque signal from the torque sensor dropping below the threshold.

21. The method of claim 20, wherein the drive output is rotated to align the drive output with the drive input of the robotic medical instrument.

22. The method of claim 21, wherein the robotic medical instrument comprises at least one pre-tensioned pull wire associated with the drive input.

23. The method of claim 20, wherein the torque signal is indicative of a direction of a torque imparted on the drive output, and wherein the method comprises activating the motor to cause rotation of the motor in a direction that is the same as the direction of the imparted torque.

24. The method of claim 20, wherein a speed of rotation of the motor is proportional to a measured torque determined based on the torque signal.

25. The method of claim 20, wherein a speed of rotation of the motor is constant.

26. The method of claim 20, wherein the drive output is a gear and the drive input is a socket.

27. The method of claim 20, wherein the drive output is a socket and the drive input is a gear.

28. The method of claim 20, wherein the activating and deactivating steps occur when in a load instrument state.

29. A robotic medical system, comprising:
    an instrument drive mechanism comprising
        a drive output configured to rotate and engage a corresponding drive input on a handle of a robotic medical instrument, wherein the robotic medical instrument comprises a pre-tensioned pull wire actuated by the drive input, and
        a motor associated with the drive output and configured to rotate the drive output, and
        a sensor configured to detect when the handle of the robotic medical instrument is within a threshold loading distance from the instrument drive mechanism; and
    at least one computer-readable memory in communication with at least one processor, the memory having stored thereon computer-executable instructions that cause the at least one processor to:
        determine that the robotic medical instrument is within the threshold loading distance of the instrument drive mechanism based on an output of the sensor, and
        activate the motor associated with the drive output to cause the drive output to oscillate to facilitate alignment of the drive output and the corresponding drive input.

30. The system of claim 29, wherein the instructions further configure the processor to place the motor in an admittance mode the robotic medical instrument is within the threshold loading distance of the instrument drive mechanism.

* * * * *